(12) United States Patent
Potyrailo et al.

(10) Patent No.: US 8,318,099 B2
(45) Date of Patent: Nov. 27, 2012

(54) CHEMICAL AND BIOLOGICAL SENSORS, SYSTEMS AND METHODS BASED ON RADIO FREQUENCY IDENTIFICATION

(75) Inventors: Radislav Alexandrovich Potyrailo, Niskayuna, NY (US); William Guy Morris, Rexford, NY (US); Kenneth Brakeley Welles, II, Scotia, NY (US); Andrew Michael Leach, Clifton Park, NY (US); Andrew David Pris, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 1517 days.

(21) Appl. No.: 11/259,711

(22) Filed: Oct. 26, 2005

(65) Prior Publication Data

US 2007/0090927 A1    Apr. 26, 2007

(51) Int. Cl.
*G01N 27/00* (2006.01)
(52) U.S. Cl. ...... 422/82.02; 422/52; 422/73; 422/82.01; 422/82.08; 422/82.09; 422/82.11; 422/503; 422/504; 422/407; 422/502; 436/164; 436/177; 436/43; 436/63; 506/30; 435/29; 435/4; 435/7.1; 250/214.1; 250/251; 250/576; 530/408; 714/752
(58) Field of Classification Search ............ 422/50, 422/58, 82.01, 82.05, 52, 73, 82.08, 82.09, 422/82.11, 99, 102, 407, 501, 502, 503, 504; 436/164, 177, 43, 63; 506/30; 435/29, 4, 435/6, 7.1; 250/214.1, 251, 576; 530/408; 714/752

See application file for complete search history.

(56) References Cited

U.S. PATENT DOCUMENTS

| | | | |
|---|---|---|---|
| 6,025,725 A | 2/2000 | Gershenfeld et al. | |
| 6,359,444 B1 | 3/2002 | Grimes | |
| 6,472,987 B1 | 10/2002 | Gershenfeld et al. | |
| 6,496,102 B1 | 12/2002 | Kyrtsos | |
| 6,586,946 B2 | 7/2003 | Hefti et al. | |
| 2002/0040968 A1* | 4/2002 | Black et al. | 250/393 |
| 2005/0088299 A1* | 4/2005 | Bandy et al. | 340/539.16 |

* cited by examiner

*Primary Examiner* — Dennis M White
(74) *Attorney, Agent, or Firm* — Jean K. Testa

(57) ABSTRACT

Embodiments of the invention include a wireless sensor, such as an RFID tag, that includes a substrate, an antenna disposed on the substrate, and an environmentally sensitive sensor material disposed over at least a portion of said substrate. Other embodiments an RFID tag and at least one antibody coupled to the RFID tag. The RFID tag includes a substrate, circuitry disposed on the substrate, and an antenna coupled to the substrate. The at least one antibody is capable of affecting the signals emanating from the RFID tag. Further embodiments include a detection system that includes a reader. Yet other embodiments include a method for detecting specific analytes. The method includes providing an RFID tag which emanates a first signal having a first frequency, and enabling the REID tag to emanate a second signal having a second frequency upon attraction of a specific analyte to the RFID tag.

8 Claims, 19 Drawing Sheets

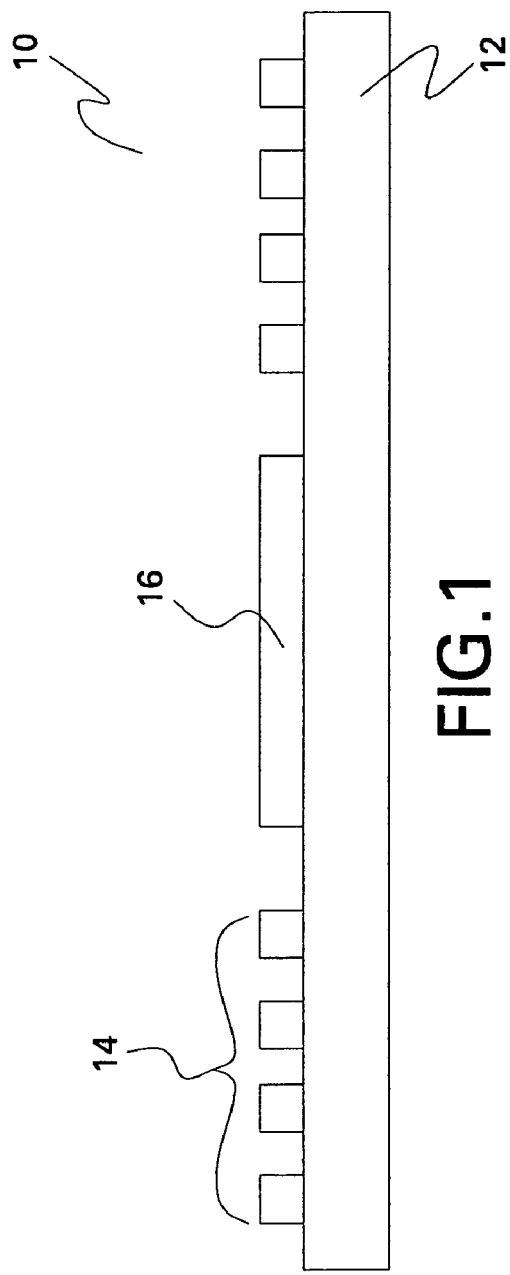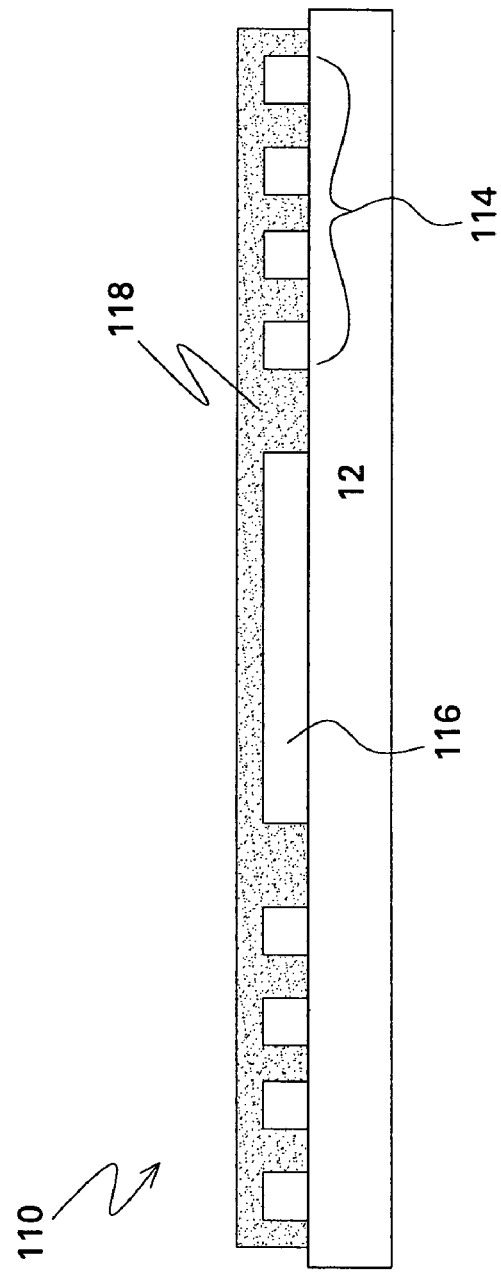

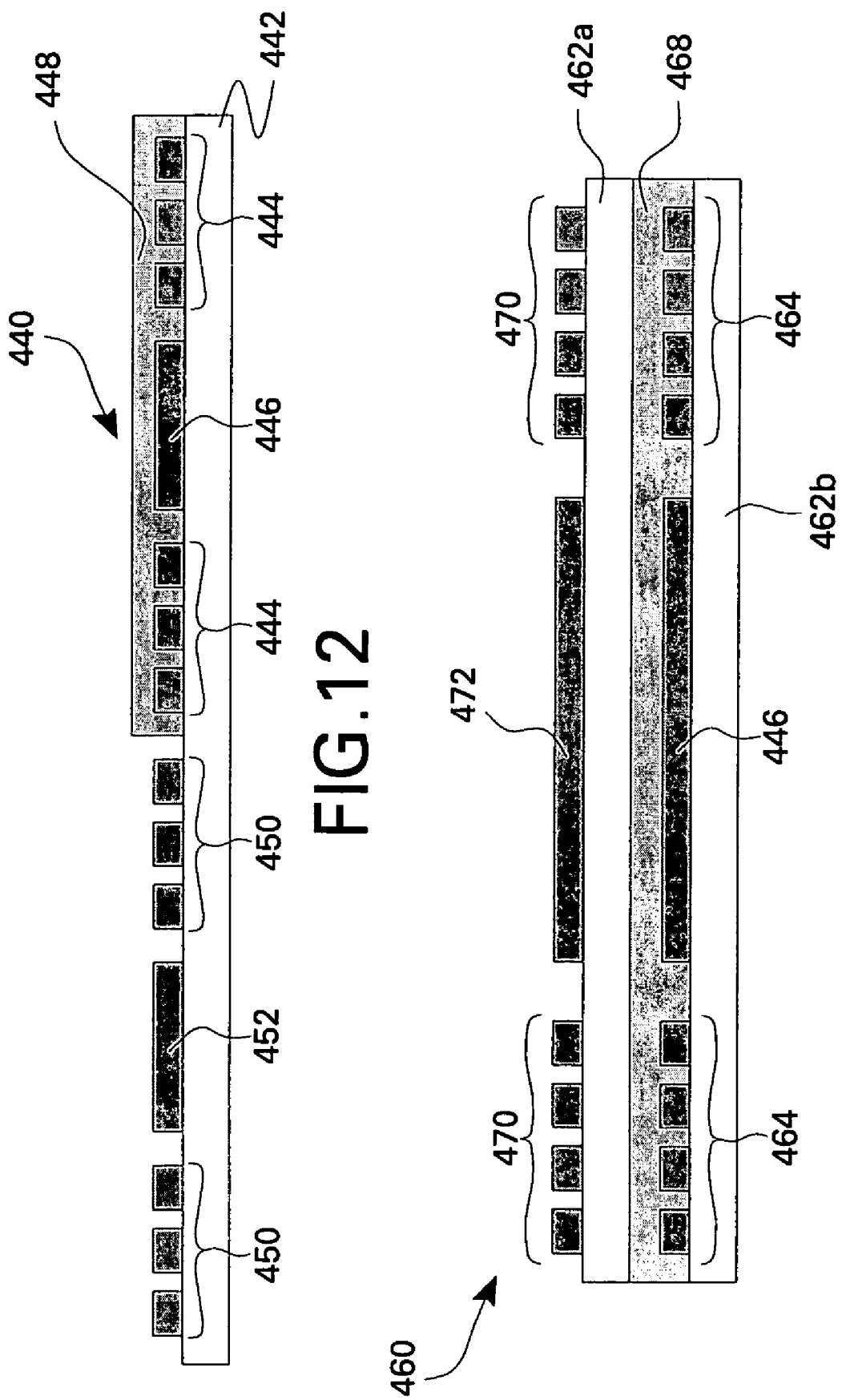

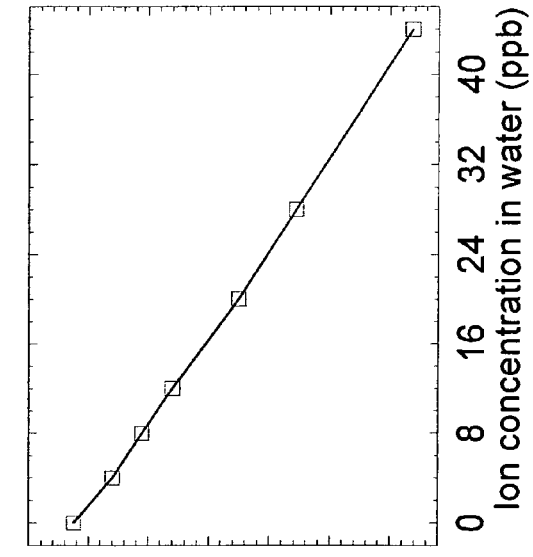
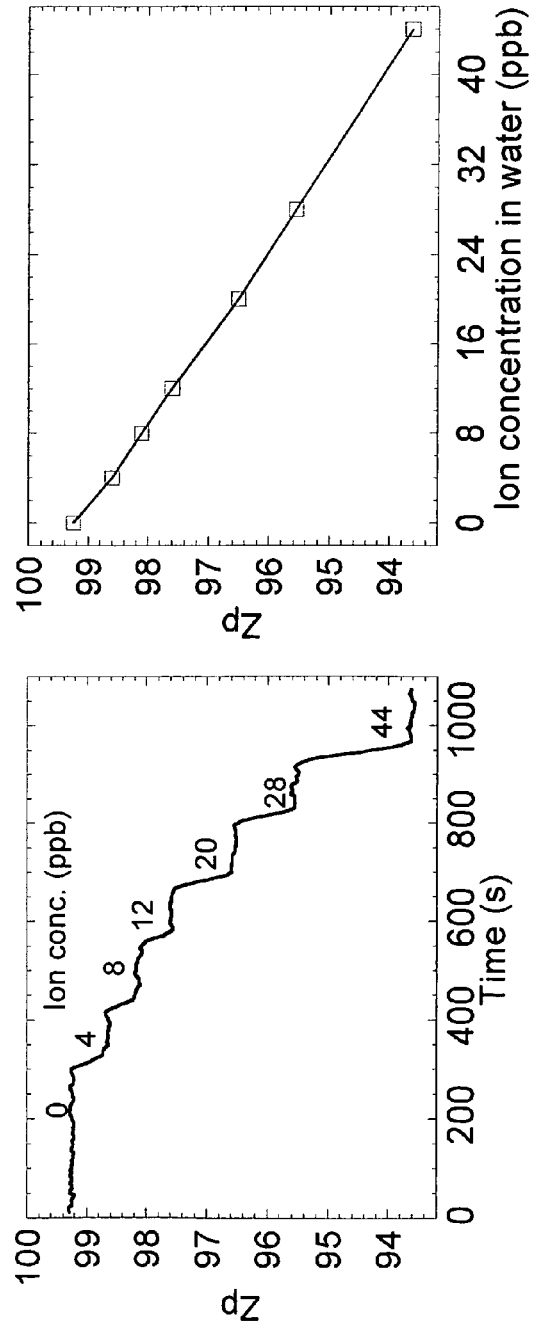
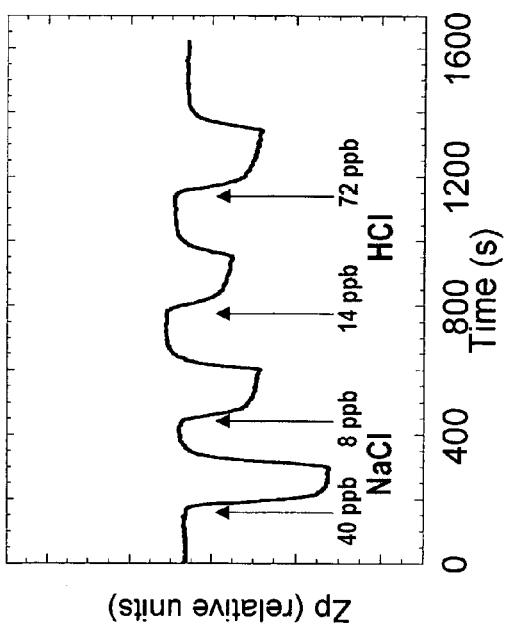
FIG. 15
FIG. 16

CHEMICAL AND BIOLOGICAL SENSORS, SYSTEMS AND METHODS BASED ON RADIO FREQUENCY IDENTIFICATION

BACKGROUND

Radio Frequency Identification (RFID) tags used in chemical or biological sensors, such as RFID tag 10 illustrated in FIG. 1, are known. Such RFID tags 10 detect signals by measuring a single parameter. RFID tag 10 includes a substrate 12 upon which are positioned an antenna 14 and a capacitor 16. As used in this patent application, an antenna is defined as a circuit that includes a resistor element, an inductance element and a capacitor element. Among the disadvantages of RFID tags 10 as chemical and/or biological sensors are difficulties in performing chemical or biological measurements in the presence of chemical and physical interferences.

Some known chemical or biological sensors include attaching an identification marker with an antibody. For example, some chemical/biological sensors include a chip attached to an antibody, wherein the chip includes a fluorescent marker identifying the specific antibody.

Some known chemical or biological sensors include structural elements that are formed from a material that selectively responds to a specific analyte. See, U.S. Pat. No. 6,359,444. Other known chemical or biological sensors include an electromagnetically active material that is located in a specific position on the sensors and that may be altered by an external condition. See, U.S. Pat. No. 6,025,725. Some known chemical or biological sensor systems include components for measuring more than one electrical parameter. See, U.S. Pat. No. 6,586,946.

In practical situations, any wireless chemical or biological sensor may not be accurately positioned with respect to a receiver antenna. Thus, the response of the wireless sensor will be affected by such position differences. The sensitivity of the sensor response (defined as a level of the sensor signal change upon exposure to a certain concentration of analyte) is dependent on the antenna-to-sensor position.

SUMMARY

One embodiment of the invention described herein is directed to a wireless sensor that includes a substrate, a radio frequency antenna disposed on the substrate, and an environmentally sensitive sensor material disposed over at least a portion of the substrate.

Another embodiment of the invention is directed to a wireless sensor including a substrate and a radio frequency antenna disposed on the substrate. The radio frequency antenna is formed of environmentally sensitive materials.

Another embodiment of the invention is directed to a detection system that includes an RFID tag and a reader for receiving and processing signals from the RFID tag. The reader is configured to measure a signal from the RFID tag and at least one additional parameter from which a signal is derived.

Another embodiment of the invention is a method for detecting specific analytes. The method includes providing a wireless sensor which emanates a first signal having a first frequency and enabling the wireless sensor to emanate a second signal having a second frequency upon attraction of a specific analyte to the wireless sensor.

These and other advantages and features will be more readily understood from the following detailed description of preferred embodiments of the invention that is provided in connection with the accompanying drawings.

BRIEF DESCRIPTION OF THE DRAWINGS

FIG. 1 is a schematic view of a known radio frequency identification tag.

FIG. 2 is a schematic view of a radio frequency identification tag constructed in accordance with an exemplary embodiment of the invention.

FIG. 12 is a schematic view of a radio frequency identification tag constructed in accordance with an exemplary embodiment of the invention.

FIG. 13 is a schematic view of a radio frequency identification tag constructed in accordance with an exemplary embodiment of the invention.

FIGS. 15A and 15B illustrate a response of an RFID tag constructed in accordance with an exemplary embodiment of the invention in water having low levels of ions.

FIG. 16 illustrates responses by an RFID tag constructed in accordance with an exemplary embodiment of the invention to variable concentrations of ions.

DETAILED DESCRIPTION OF PREFERRED EMBODIMENTS

Figure 3:
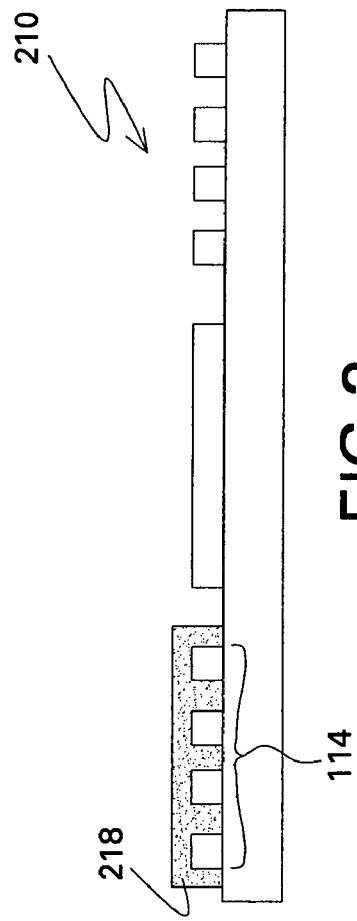
FIG. 3 is a schematic view of a radio frequency identification tag constructed in accordance with an exemplary embodiment of the invention.

Referring to FIG. 2, there is illustrated a wireless sensor 110 constructed in accordance with an exemplary embodiment of the invention. The wireless sensor 110 may be a radio frequency identification (RFID) tag. A wide variety of commercially available tags can be applied for the deposition of sensor structures. These tags operate at different frequencies ranging from about 125 kHz to about 2.4 GHz. Suitable tags are available from different suppliers and distributors, for example, Texas Instruments, Digi Key, Amtel, Hitachi, and others. Suitable tags can operate in passive, semi-passive and active modes. The passive RFID tag does not need a power source for operation, while the semi-passive and active RFID tags rely on the use of onboard power for their operation.

The wireless sensor 110 includes a chip or substrate 12, upon which is disposed an antenna 114 and a capacitor 116. An environmentally sensitive sensor material 118 may be disposed in the form of a coating. Specifically, the environmentally sensitive sensor material 118 is disposed adjacent to the substrate 12 and the antenna 114. By "adjacent to", what is meant is in the immediate vicinity of, including, for example, over, on, abutting, co-terminus with, proximal to, nearby, or, at least in the instance of the antenna 114, in such proximity as to produce an effect on the antenna 114. The environmentally sensitive sensor material 118 is further disposed in such proximity with capacitor 116 that it produces an effect on the capacitor, for example, between the plates of the capacitor 116. The environmentally sensitive sensor material 118 includes chemical or biological materials. For example, the environmentally sensitive sensor material 118 may include conductive sensor materials such as inorganic, polymeric, biological, metallic, semiconducting, or structured materials. Further, the environmentally sensitive sensor material 118 may include composite sensor materials, such as materials where a base material is blended with a conductive soluble or insoluble additive. The additive may be in a form of particles, fibers, flakes, or other form suitable for providing electrical conductance. Also, the environmentally sensitive sensor material 118 may be formed of any other materials, such as, for example, molecules, biospecific entities, cells, or solid support materials that are capable of affecting the electrical environment in the immediate vicinity when appropriately stimulated.

Referring to FIG. 3, there is illustrated a wireless sensor 210. An environmentally sensitive sensor material 218 is positioned over a portion of an antenna 114. The environmentally sensitive sensor material 218 includes chemical and biological materials used to modulate antenna electrical properties. Examples of the chemical and biological materials may include conductive sensor materials such as inorganics, polymerics, and others. Alternatively, the antenna 114 may be formed from chemical and biological sensitive materials. Deposition of an antenna 114 formed of such materials may be performed using arraying, ink-jet printing, screen printing, vapor deposition, spraying, draw coating, and any other suitable deposition methods.

As a further alternative, the antenna 114 may be formed of environmentally sensitive materials, such as, for example, materials sensitive to pH, $CO_2$, and/or $O_2$, and immediately adjacent to the antenna 114 is disposed a cell culture friendly material. As cell growth occurs, the chemical composition of the environment immediately surrounding this cell culture region, including the antenna 114, changes, resulting in a change in the power gathering efficiency of the antenna 114. Possible applications for such a wireless sensor 210 include food quality monitoring, environmental monitoring, first responders, industrial monitoring, work-place monitoring, medical monitoring, pharmaceutical validation, residential monitoring, and experimental cell biology. Measurements may be performed of gaseous, liquid, and solid environments.

Figure 4:
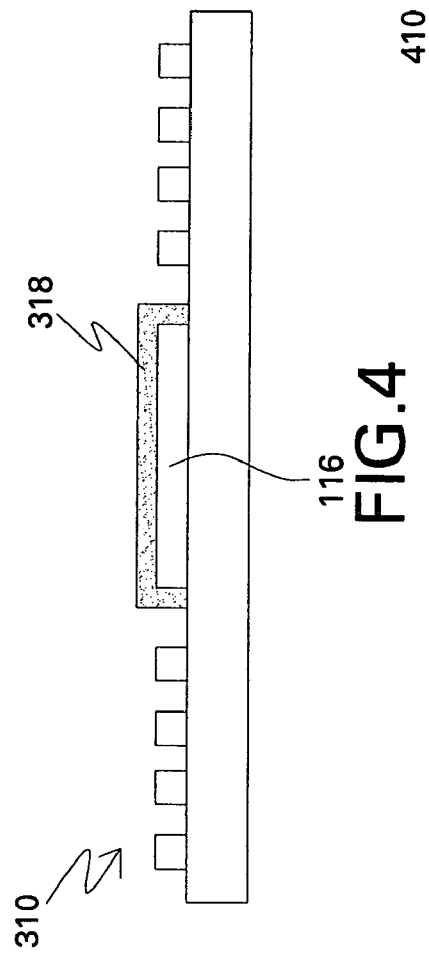
FIG. 4 is a schematic view of a radio frequency identification tag constructed in accordance with an exemplary embodiment of the invention.

Referring to FIG. 4, an environmentally sensitive sensor material 318 is disposed in such proximity with a capacitor 116 that it produces an effect on the capacitor, for example, between the plates of the capacitor 116, of a wireless sensor 310. Alternatively, the capacitor 116 may be fabricated from materials that are environmentally sensitive. One fabrication method may include micro patterning of a thin film coupled with deposition of the chemical and biological sensitive materials and electrodes.

In another embodiment, chemical and/or biological sensitive materials are used as part of a reflector to modulate reflector properties. The modulated properties may include, for example, the frequency and/or the intensity of the reflected RF signal. In this embodiment, the chemical and/or biological sensitive materials change their electrical properties such that RF energy directed at them is reflected back in a modified form. One example may include a metal plate covered with a material whose resistance varies with the sensed quantity. Without any of the sensed quantity, the material serves as an insulator, so that RF directed towards it passes through it and is reflected by the metal plate (or foil) underneath. In such an instance, a strong reflected signal is given off having a certain phase relationship to the transmitted signal. When activated by a sensed quantity, the material becomes resistive, and dissipates the RF energy directed at it. In such an instance, the amplitude of the reflected RF signal is reduced and the phase relationship to the transmitted signal is changed.

Figure 5:
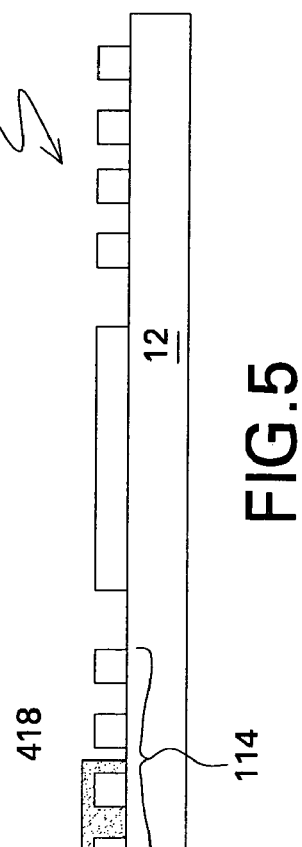
FIG. 5 is a schematic view of a radio frequency identification tag constructed in accordance with an exemplary embodiment of the invention.

As shown in FIG. 5, environmentally sensitive sensor material may be disposed over only a portion of the antenna. As illustrated, a wireless sensor 410 includes an antenna 114 that is partially covered by an environmentally sensitive sensor material 418. In one embodiment of the wireless sensor 410, the environmentally sensitive sensor material 418 serves to adjust and/or modulate the geometry of the antenna 114 upon a positive interaction with an analyte species. The environmentally sensitive sensor material 418 is deposited upon the substrate 12 in a known arrangement using a known deposition method, such as, for example, arraying, ink-jet printing, screen printing, vapor deposition, spraying, or draw coating. Upon a positive chemical and/or biological interaction with a specified analyte, the geometry of the antenna 114 is altered through deposition or removal of material from the antenna 114 through, for example, electrochemical, photochemical, biochemical, or biological techniques. The deposition or removal of the material will, in all instances, result in a change in the response of the wireless sensor 410. For example, a biospecific entity, i.e., a peptide, nucleic acid, or antibody, may be patterned upon the antenna 114. A traditional sandwich assay, or other assay known in the art, may then be performed. A sample is exposed to the test sample and a labeling moiety that possesses a gold nanoparticle is employed. If the analyte of interest is present, the bio-recognition will result in gold nanoparticles existing in the pre-established arrangement of the biospecific entity. If the antenna 114 is not adjusted adequately, silver staining may be performed to create a thin film of silver in the pattern as defined by the biospecific entity. The silver staining will affect the RF response.

The term "peptide" refers to oligomers or polymers of any length wherein the constituent monomers are alpha amino acids linked through amide bonds, and the term encompasses amino acid dimers as well as polypeptides, peptide fragments, peptide analogs, naturally occurring proteins, mutated, variant or chemically modified proteins, fusion proteins, and the like. The amino acids of the peptide molecules may be any of the twenty conventional amino acids, stereoisomers (e.g., D-amino acids) of the conventional amino acids, structural variants of the conventional amino acids, e.g., isovaline, or non-naturally occurring amino acids such as α,α-disubstituted amino acids, N-alkyl amino acids, β-alanine, naphthylalanine, 3-pyridylalanine, 4-hydroxyproline, O-phosphoserine, N-acetylserine, N-formylmethionine, 3-methylhistidine, 5-hydroxylysine, and nor-leucine. In addition, the term "peptide" encompasses peptides with post-translational modifications such as glycosylations, acetylations, phosphorylations, and the like. The term "oligonucleotide" is used herein to include a polymeric form of nucleotides of any length, either ribonucleotides or deoxyribonucleotides. This term refers only to the primary structure of the molecule. Thus, the term includes triple-, double-, and single-stranded DNA, as well as triple-, double-, and single-stranded RNA. It also includes modifications, such as by methylation and/or by capping, and unmodified forms of the oligonucleotide. More particularly, the term includes polydeoxy-ribonucleotides (containing 2-deoxy-D-ribose), polyribonucleotides (containing D-ribose), any other type of polynucleotide which is an N- or C-glycoside of a purine or pyrimidine base, and other polymers containing normucleotidic backbones, for example, polyamide (e.g., peptide nucleic acids (PNAs)) and polymorpholine (commercially available from the Anti-Virals, Inc., Corvallis, Oreg., as Neugene) polymers, and other synthetic sequence-specific nucleic acid polymers, provided that the polymers contain nucleobases in a configuration that allows for base pairing and base stacking, such as is found in DNA and RNA. There is no intended distinction in length between the terms "polynucleotide", "oligonucleotide", "nucleic acid" and "nucleic acid molecule", and these terms refer only to the primary structure of the molecule. Thus, these terms include, for example, 3'-deoxy-2',5'-DNA, oligo-deoxyribonucleotide N3'P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. Further included are locked nucleic acids.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

Furthermore, modifications to nucleotidic units include rearranging, appending, substituting for, or otherwise altering functional groups on the purine or pyrimidine base that form hydrogen bonds to a respective complementary pyrimidine or purine. The resultant modified nucleotidic unit optionally may form a base pair with other such modified nucleotidic units but not with A, T, C, G or U. Basic sites may be incorporated which do not prevent the function of the polynucleotide. Some or all of the residues in the polynucleotide can optionally be modified in one or more ways.

The term "antibody" as used herein includes antibodies obtained from both polyclonal and monoclonal preparations, as well as: hybrid (chimeric) antibody molecules (see, for example, Winter et al. (1991), Nature, volume 349, pp. 293-299; and U.S. Pat. No. 4,816,567); F(ab')2 and F(ab) fragments; Fv molecules (noncovalent heterodimers, see, for example, Inbar et al. (1972), Proc. Natl. Acad. Sci. USA, volume 69, pp. 2659-2662; and Ehrlich et al. (1980), Biochem., volume 19, pp. 4091-4096); single-chain Fv molecules (sFv) (see, e.g., Huston et al. (1988), Proc. Natl. Acad. Sci. USA, volume 85, pp. 5879-5883); dimeric and trimeric antibody fragment constructs; minibodies (see, e.g., Pack et al. (1992), Biochem., volume 31, pp. 1579-1584; Cumber et al. (1992), J. Immunology, volume 149B, pp. 120-126); humanized antibody molecules (see, e.g., Riechmann et al. (1988), Nature, volume 332, pp. 323-327; Verhoeyan et al. (1988), Science, volume 239, pp. 1534-1536; and U.K. Patent Publication No. GB 2,276,169, published 21 Sep. 1994); and, any functional fragments obtained from such molecules, wherein such fragments retain specific-binding properties of the parent antibody molecule.

In another embodiment, the antenna 114 is modified by including throughout the antenna 114 or in only portions thereof entities displaying a metallic nanoparticle. Utilizing standard assays, the presence of an analyte in a test sample will result in a change in the RF geometry and in the removal of the metallic nanoparticles. One possible aspect of this embodiment includes the metallic nanoparticles displaying a bio-entity that includes a nucleic acid strand and the analyte being a restriction enzyme. Upon interaction between the analyte and the test substrate 12, the enzyme will cleave the nucleic acid and result in removal of the metallic nanoparticle.

Figure 6:
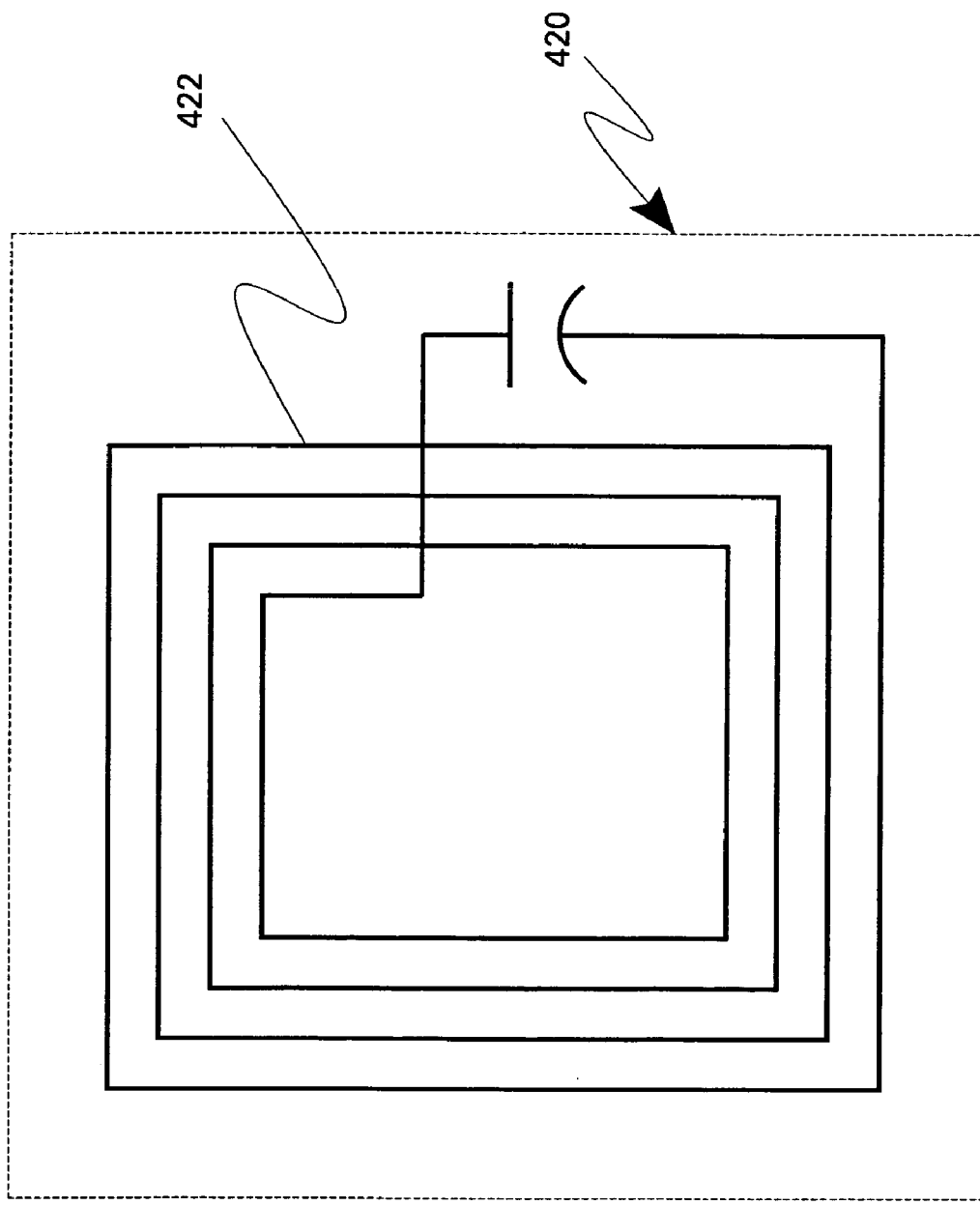
FIG. 6 is a schematic view of a resonant antenna circuit constructed in accordance with an exemplary embodiment of the invention.

While several embodiments of wireless sensors are illustrated, it should be appreciated that other embodiments are within the scope of the invention. For example, circuitry contained on the wireless sensor may utilize power from the illuminating RF energy to drive a high Q resonant circuit, such as the circuit 422 within the capacitance based sensor 420 illustrated in FIG. 6. The high Q resonant circuit 422 has a frequency of oscillation determined by the sensor 420 to which it is connected. As illustrated, the sensor 420 incorporates a capacitor whose capacitance varies with the sensed quantity. The illuminating RF energy may be varied in frequency, and the reflected energy of the sensor is observed. Upon maximizing the reflected energy, a resonant frequency of the circuit 422 is determined. The resonant frequency may then be converted into a measurement of the sensor 420 on the circuit 422.

Figure 7:
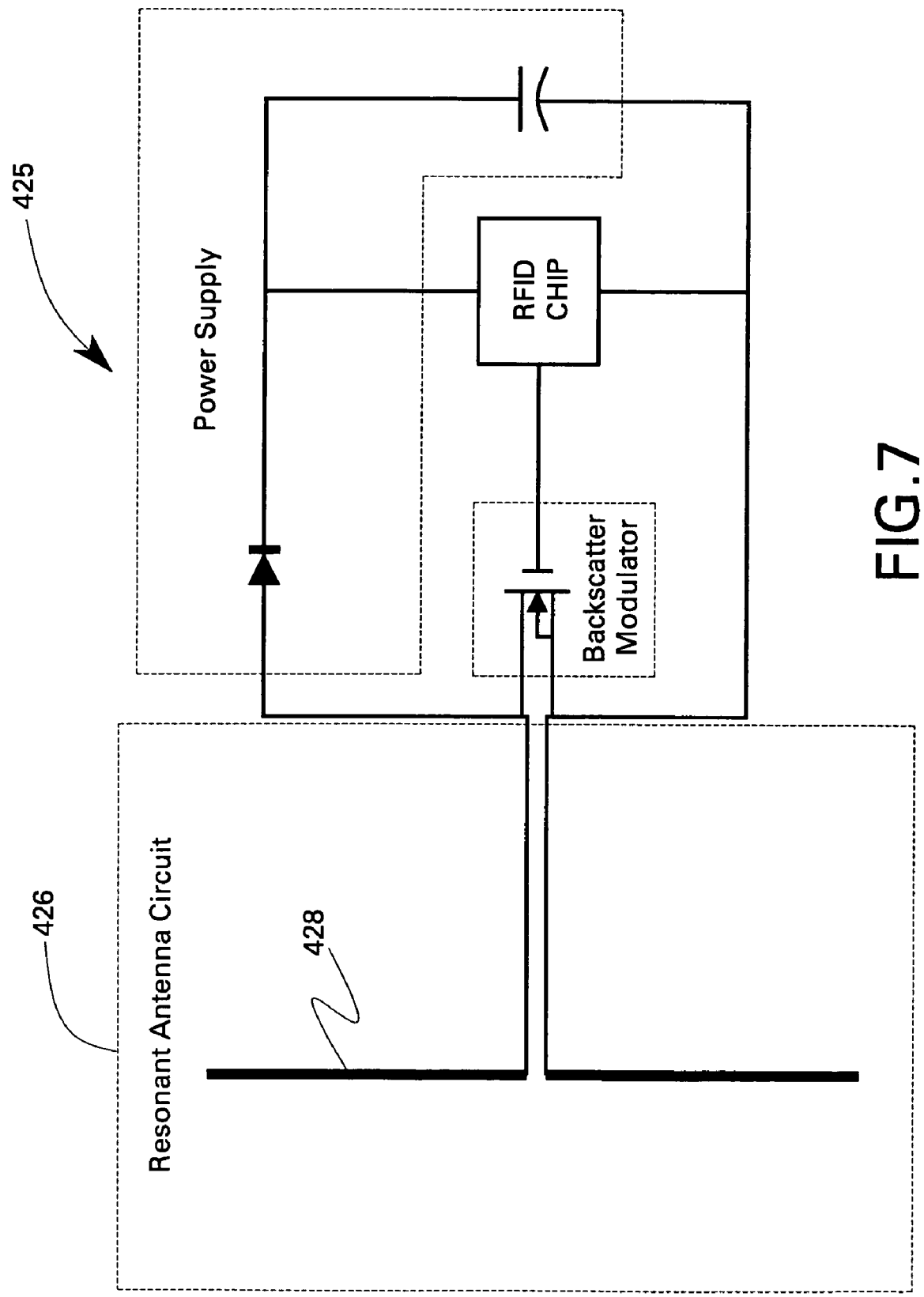
FIGS. 7-8 are schematic views of circuitry for RFID systems constructed in accordance with exemplary embodiments of the invention.
Figure 8:
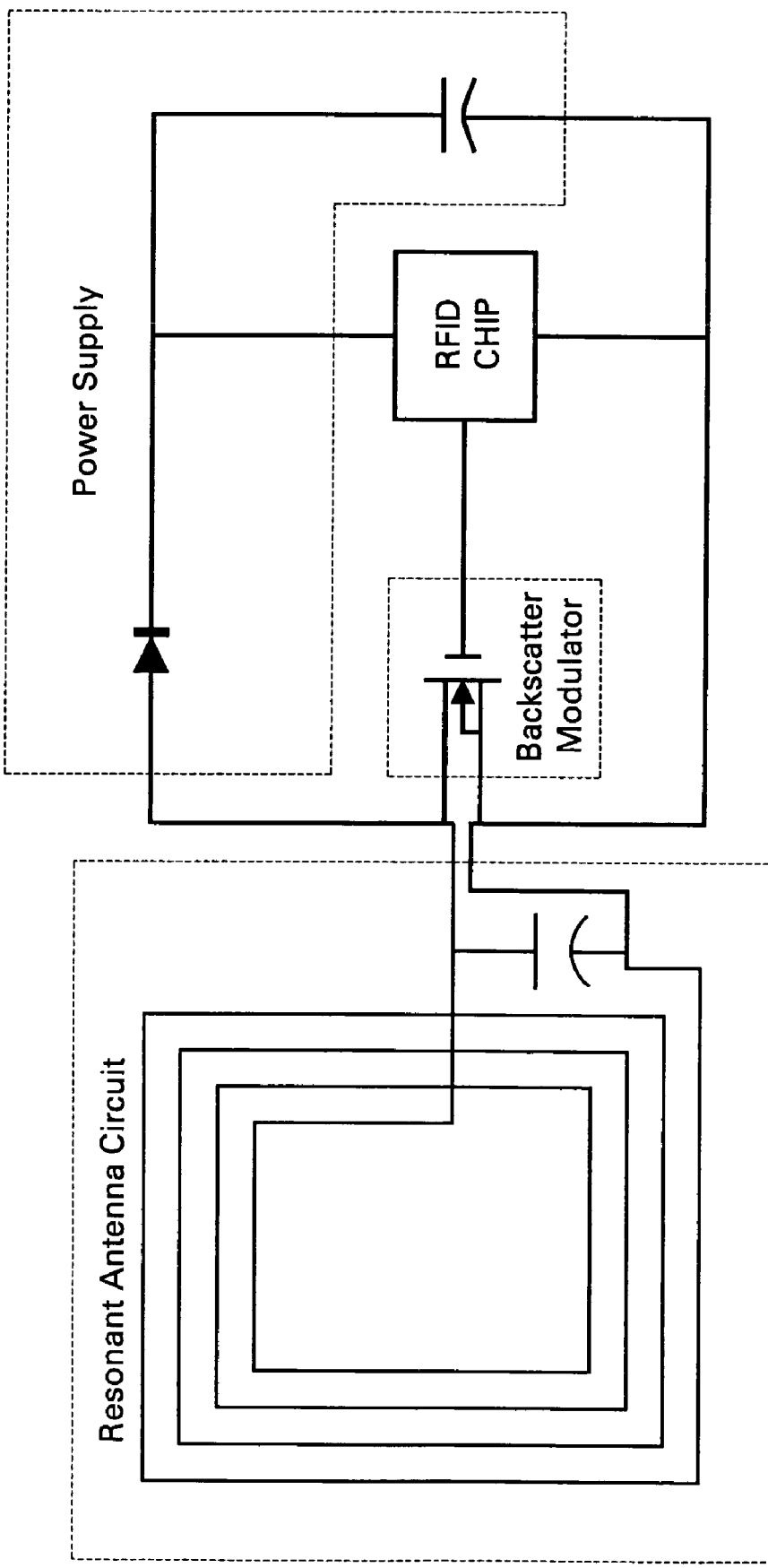
Figure 9:
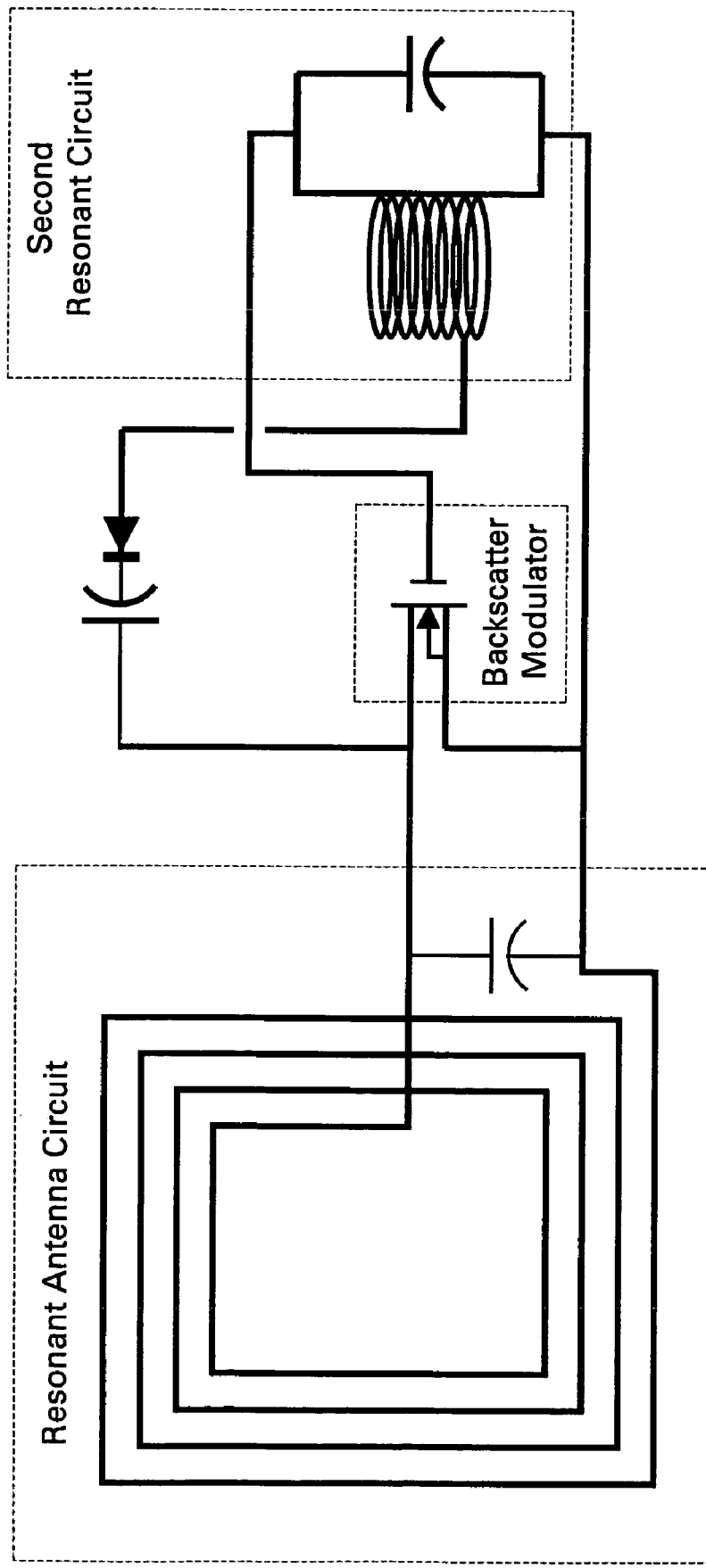
FIGS. 9-11 are schematic views of circuitry for wireless sensors constructed in accordance with exemplary embodiments of the invention.
Figure 10:
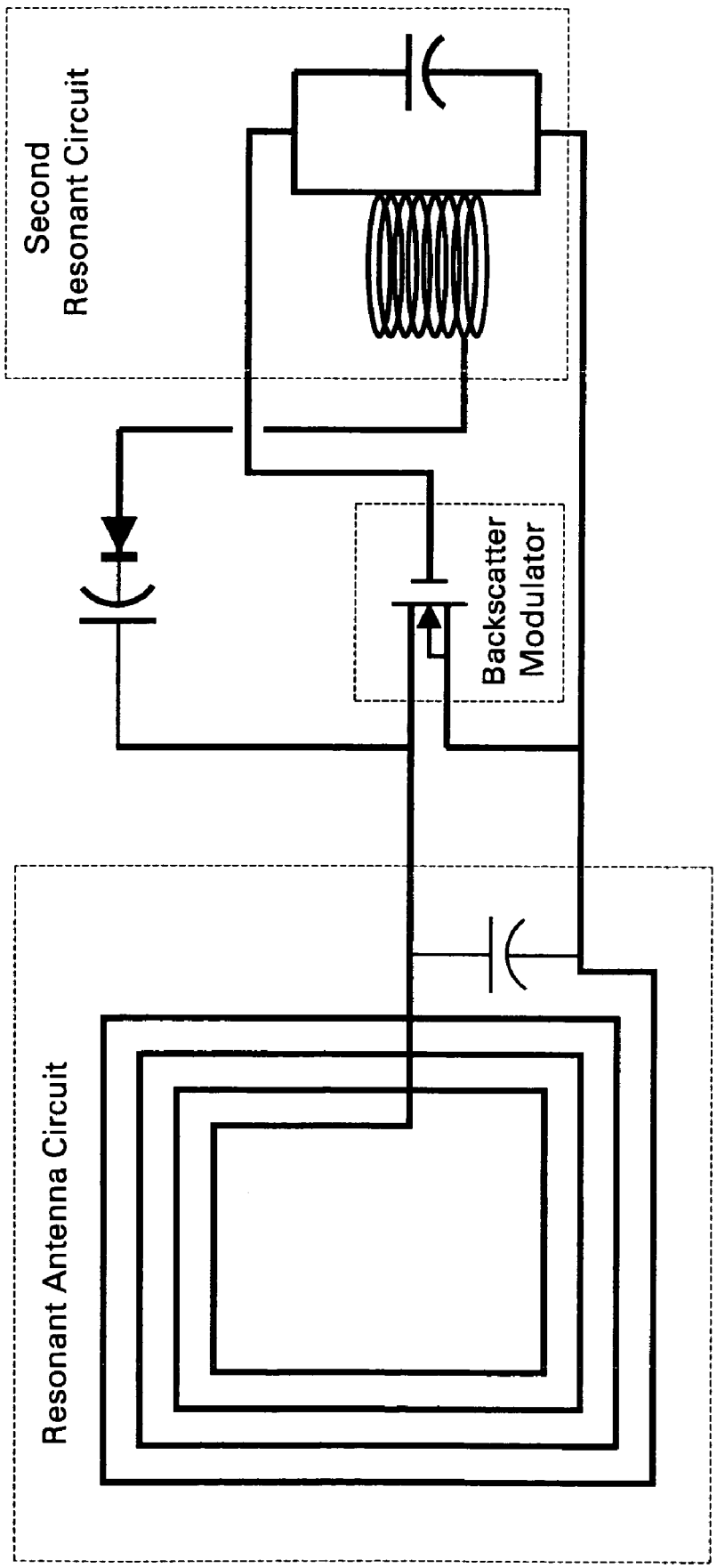
Figure 11:
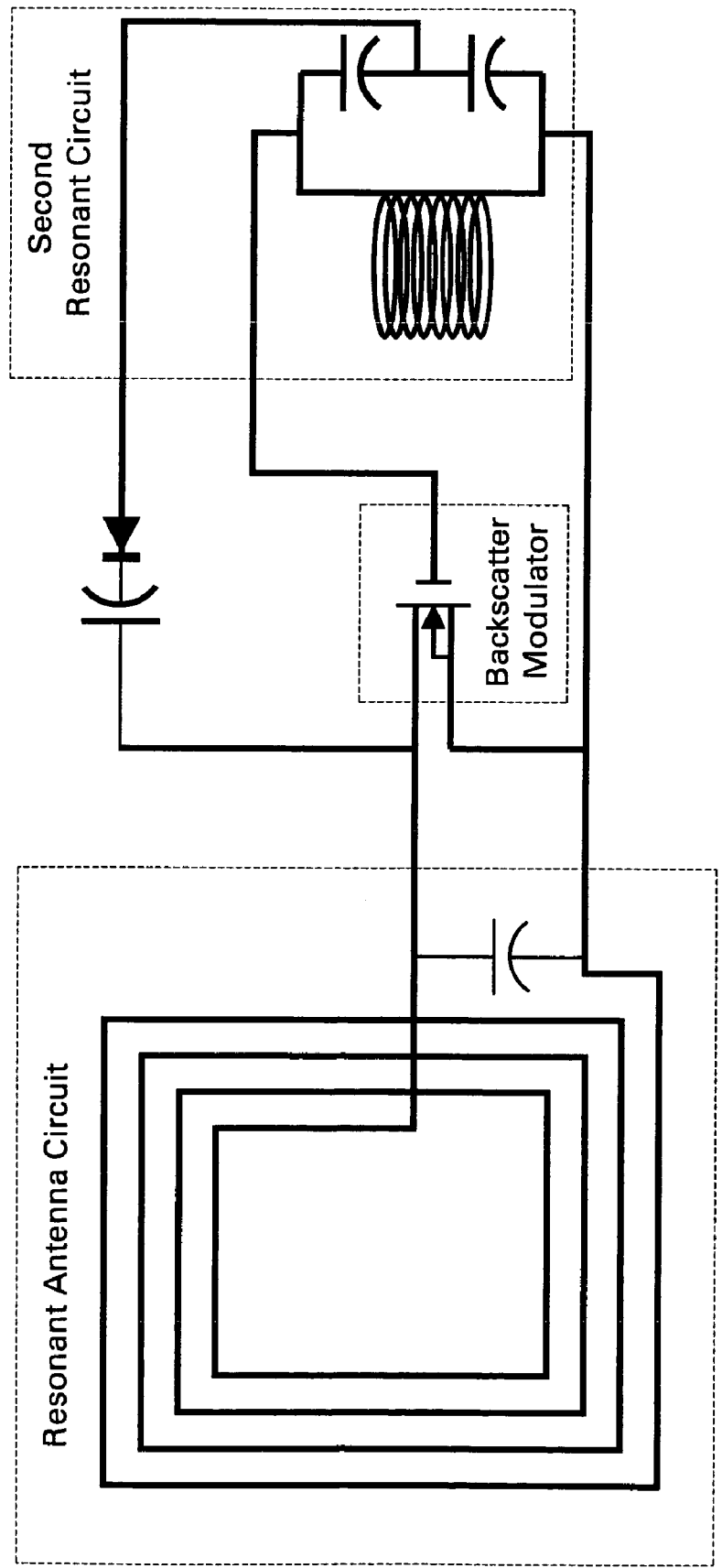

In other embodiments, illuminating RF energy is pulsed at a certain repetitive frequency close to the resonant frequency of a high Q oscillator. For example, as illustrated in FIG. 7, the pulsed energy is rectified in a wireless sensor 425 and is used to drive a high Q resonant circuit 426 having a resonant frequency of oscillation determined by the sensor 425 to which it is connected. After a period of time, the pulsed RF energy is stopped and a steady level of illuminating RF energy is transmitted. The high Q resonant circuit 426 is used to modulate the impedance of the antenna 428 using the energy stored in the high Q resonant circuit 426. A reflected RF signal is received and examined for sidebands. The frequency difference between the sidebands and the illuminating frequency is the resonant frequency of the circuit 426. The resonant frequency is then converted into a measurement of the sensor 425 on the resonant circuit 426. FIGS. 8-11 illustrate various other embodiments of wireless sensors used for driving high Q resonant circuits. As shown in FIGS. 9-11, wireless sensors may include both a resonant antenna circuit and a sensor resonant circuit, which may include an LC tank circuit. The resonant frequency of the antenna circuit is a higher frequency than the resonant frequency of the sensor circuit, for example, as much as four to 1000 times higher. The sensor circuit has a resonant frequency that may vary with some sensed environmental condition. The two resonant circuits may be connected in such a way that when alternating current (AC) energy is received by the antenna resonant circuit, it applies direct current energy to the sensor resonant circuit. As shown in FIG. 9, the AC energy may be supplied through the use of a diode and capacitor, and the AC energy may be transmitted to the sensor resonant circuit through the LC tank circuit through either a tap within the L of the LC tank circuit or a tap within the C of the LC tank circuit. Further, the two resonant circuits may be connected such that voltage from the sensor resonant circuit may change the impedance of the antenna resonant circuit. As shown in FIG. 9, the modulation of the impedance of the antenna circuit may be accomplished through the use of a transistor, for example a FET.

Alternatively, illuminating RF energy is pulsed at a certain repetitive frequency. The pulsed energy is rectified in a wireless sensor (FIGS. 7-11) and is used to drive a high Q resonant circuit having a resonant frequency of oscillation determined by the sensor to which it is connected. After a period of time, the pulsed RF energy is stopped and a steady level of illuminating RF energy is transmitted. The resonant circuit is used to modulate the impedance of the antenna using the energy stored in the high Q resonant circuit. A reflected RF signal is received and examined for sidebands. The process is repeated for multiple different pulse repetition frequencies. The pulse repetition frequency that maximizes the amplitude of the sidebands of the returned signal is determined to be the resonant frequency of the resonant circuit. The resonant frequency is then converted into a measurement of the sensor on the resonant circuit.

Referring to FIG. 12, a two-channel RFID sensor 440 is illustrated. The sensor 440 includes a substrate 442 upon which are disposed an analyte responsive RFID and an analyte unresponsive RFID. The analyte unresponsive RFID includes a first channel antenna 444 and a first capacitor 446 that are not responsive to environmental changes. The first channel antenna 444 and the first capacitor 446 may be covered with an inert material 448. The analyte responsive RFID includes a second channel antenna 450 and a second capacitor 452 that are constructed from environmentally sensitive material. The first channel antenna 444 provides a measure of the power being received from an external reader, while the second channel antenna 450 provides a combination of information, including the magnitude of received power and the environmental conditions. In this format, the first channel antenna 444 serves as a reference for the second channel antenna 450, allowing for improved quantitative measurements, and less susceptibility to errors induced by the distance between the sensor 440 and the reader.

Referring to FIG. 13, there is shown a two-channel RFID sensor 460. The sensor 460 includes a pair of stacked substrates 462a, 462b upon which are disposed, respectively, an analyte responsive RFID and an analyte unresponsive RFID. The analyte unresponsive RFID includes a first channel antenna 464 and a first capacitor 466 that are not responsive to environmental changes. The first channel antenna 464 and the first capacitor 466 may be covered with an inert material 468. The analyte responsive RFID includes a second channel antenna 470 and a second capacitor 472 that are constructed from environmentally sensitive material. The first channel antenna 464 provides a measure of the power being received from an external reader, while the second channel antenna 470 provides a combination of information, including the magnitude of received power and the environmental conditions. In this format, the first channel antenna 464 serves as a reference for the second channel antenna 470, allowing for improved quantitative measurements, and less susceptibility to errors induced by the distance between the sensor 460 and the reader.

Figure 14:
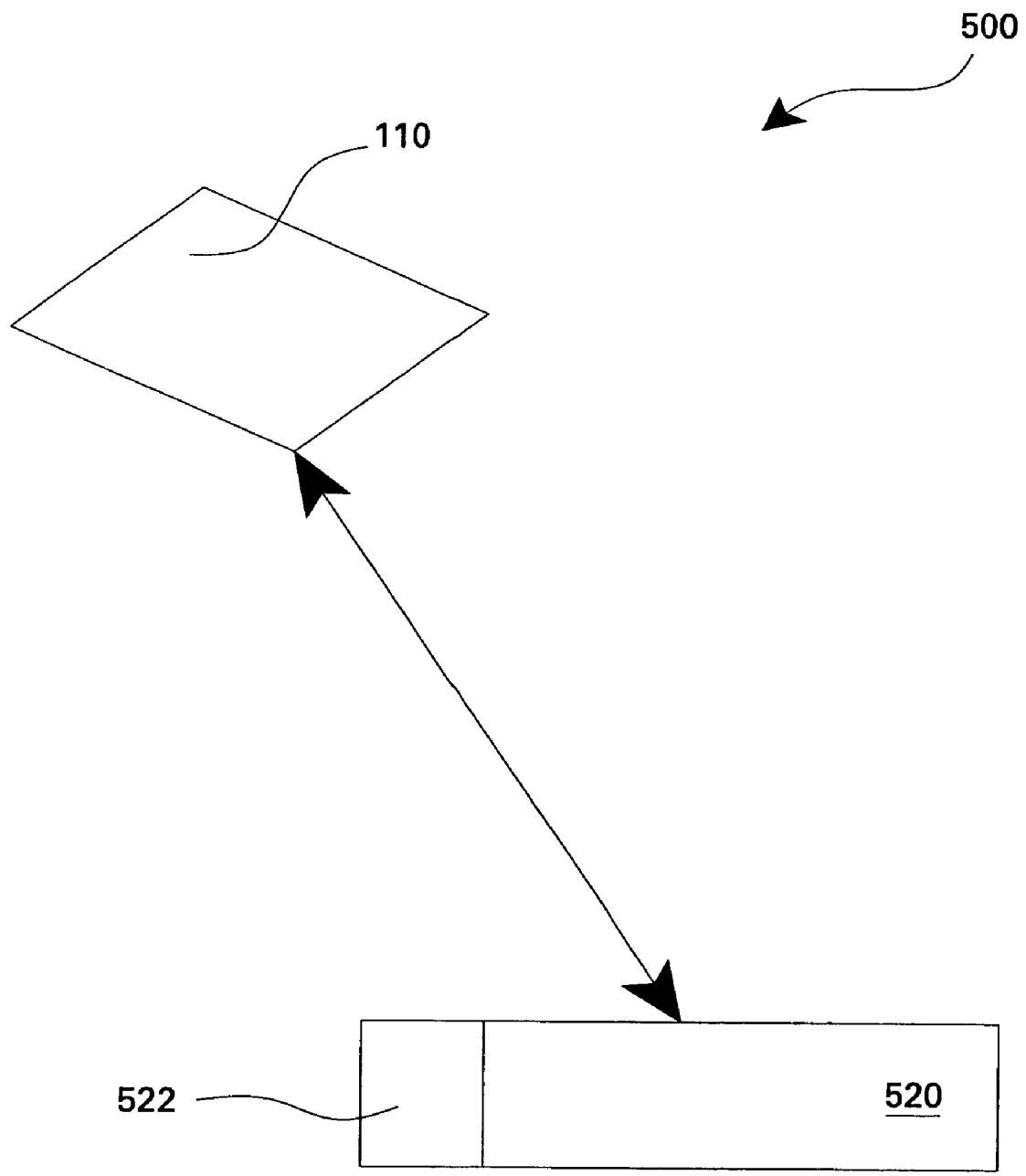
FIG. 14 is a schematic representation of a detection system constructed in accordance with an exemplary embodiment of the invention.

With specific reference to FIG. 14, there is shown a detection system 500 including a coated wireless sensor 110 and a reader 520. It should be appreciated that any of the wireless sensors described with reference to FIGS. 2-11 may be included within the detection system 500. The reader 520 includes a pattern recognition subcomponent 522. In one embodiment of the system 500, the distance d between the wireless sensor 110 and the reader 520 is kept constant. The reader 520 periodically measures the reflected RF signal from the wireless sensor 110. Periodic measurements from the same wireless sensor 110 provide information about the rate of change of a sensor signal, which is related to the status of the chemical/biological environment surrounding the wireless sensor 110. In the illustrated embodiment, the reader 520 is configured to both read and quantify the intensity of the signal from the wireless sensor 110. Non-limiting examples of applications for such a system 500 include detection of food quality change on supermarket shelves, detection of food quality change in refrigerators, monitoring of bedside patients, and other applications where a stationary sensor is located for a period of several measurements with a reader.

The detection system 500 may further include a remote transceiver that is enabled to transmit energy at about the frequency of the antenna resonant frequency (FIGS. 9-11) and receives the backscatter energy at the same frequency. Specifically, the remote transceiver sends out a series (one or more) of frequency bursts at a high energy level and at the frequency of the antenna resonant circuit. The repetition rate of the burst transmission is about the resonant frequency of the sensor resonant circuit. The transceiver then stops sending high energy bursts and sends low energy continuous frequency signals at about the resonant frequency of the resonant antenna circuitry. The transceiver reads the modulated backscatter of the transmitted frequency. The frequency of the modulation of the backscatter energy is the resonant frequency of the sensor resonant circuit, which is indicative of the remotely sensed environmental condition.

EXAMPLE 1

Operation in Water

Passive wireless sensors operating with a nominal frequency of 13.5 MHz were obtained from commercial sources. For analysis of species in water, a polymer film was deposited onto the antenna circuit. A polymer, specifically poly(hydroxyethylmethacrylate), was obtained from Aldrich. In another application, a protective layer on the antenna circuit was partially removed. Variable concentrations of NaCl and HCl were made in deionized water. Measurements were performed using a network analyzer.

FIG. 15A illustrates the response of the wireless sensor in water to low ppb levels of ions (such as NaCl). A calculated detection limit (at S/N=3) was 470 part-per-trillion. Reversibility of response of the wireless sensor to variable concentrations of ions is illustrated in FIG. 15B, where replicate exposures to about 600 ppb (two replicates) and 1000 ppb (three replicates) of NaCl were made.

Response of a polymer-coated wireless sensor is depicted in FIG. 16. A polymer, specifically poly(hydroxyethylmethacrylate), was obtained from Aldrich. For deposition, the polymer was dissolved and a solution of the polymer was applied onto the wireless sensor. The sensor was exposed to NaCl and HCl at concentrations in the ranges of about 8-40 ppb (NaCl) and about 14-72 ppb (HCl). The sensor demonstrated a completely reversible response.

Figure 17:
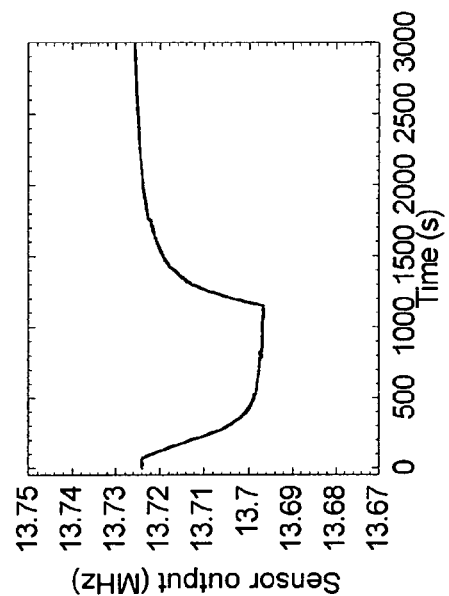
FIG. 17 illustrates a calibration curve for detecting acetone in water.

When the wireless sensor was coated with a silicone adhesive as a sorbing film for dissolved solvents in water, the sensor reversibly responded to dissolved solvents. For example, a calibration curve for detection of acetone in water is presented in FIG. 17.

EXAMPLE 2

Operation in Air

Figure 18:
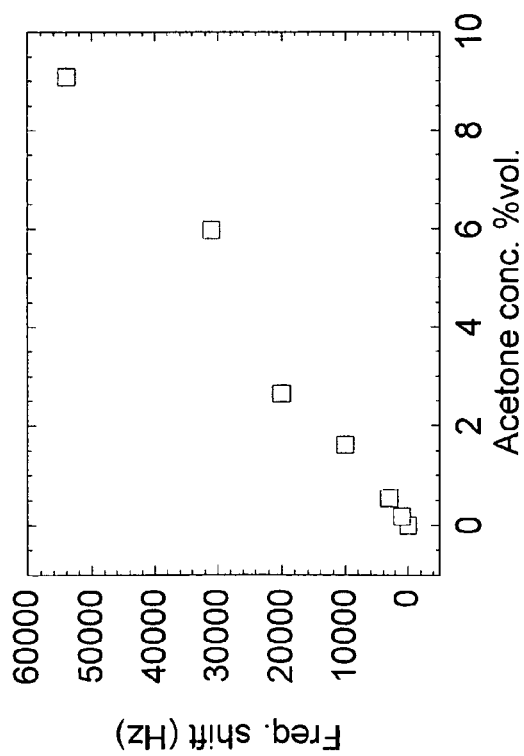
FIG. 18 illustrates a reversible response of an RFID tag constructed in accordance with an exemplary embodiment of the invention in air to low levels of toluene vapor.

Passive wireless sensors operating with a nominal frequency of 13.5 MHz were obtained from commercial sources. For analysis of species in air, a silicone polymer film was used and deposited onto the antenna circuit. Different vapors were generated using a micro pump and a set of bubblers. Measurements were performed using a network analyzer. FIG. 18 illustrates a reversible response of the tag in air to low concentration of toluene vapor (1.5% vol. in air). As illustrated, the observed signal change in FIG. 18 was from 13724000 Hz in air to 13696700 Hz in 1.5% vol. of toluene in air. Sensor sensitivity is defined as a level of the sensor signal change upon exposure to a certain concentration of analyte. Thus, the sensitivity of the sensor was (13724000-13696700)/1.5=18200 Hz/% vol. toluene.

EXAMPLE 3

Operation as a Sensor Array

Figure 19:
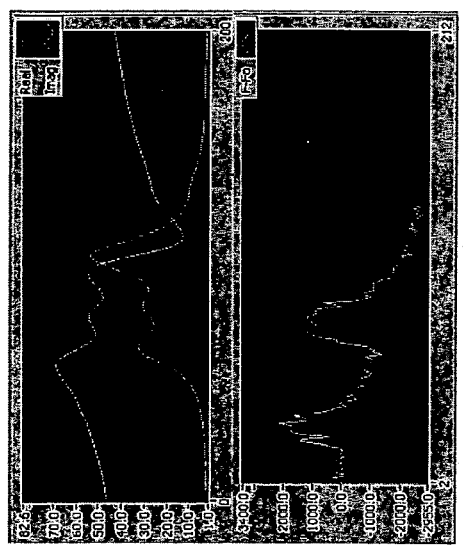
FIG. 19A illustrates real and imaginary components of a response showing discrimination between four RFID tags constructed in accordance with an exemplary embodiment of the invention.
FIG. 19B illustrates a response of one of the RFID tags constructed in accordance with an exemplary embodiment of the invention to periodic exposures to toluene vapor.

Four passive wireless sensors operating with a nominal frequency of 13.5 MHz were arranged in close proximity and measurements were performed with a single pick-up coil using a network analyzer. FIGS. 19A and 19B illustrate a clear discrimination of signals from all four wireless sensors. Specifically, FIG. 19A illustrates real and imaginary components of the response showing discrimination between four sensors, while FIG. 19B illustrates a response of one of the sensors (that sensor was chemically sensitive) to periodic exposures to toluene vapor.

Embodiments of the invention relate to methods of signal analysis from wireless sensors when used as chemical and biological sensors. Conventionally, signal detection from wireless sensors has been performed by measuring a single parameter. Embodiments of the invention demonstrate that by measuring several parameters at once, improved sensor performance is obtained and the sensor is less affected by other factors not related to the changes in chemical or biological parameters of interest. RFID systems have been recently applied for wireless sensing applications. For example, RFID-based temperature sensors are available from KSW Microtec. Bacterial sensor RFID tags are also known. The most prominent limitations of those sensors are difficulties in chemical and biological measurements in presence of chemical and physical interferences. These limitations come from measurements of only limited number of output parameters from the sensors.

Embodiments of the invention enable a way for generating signals from wireless sensors that have reduced responses due to interferences. The interferences may arise from a variety of sources, including chemical, biological, and physical interferences. The ability to provide accurate data improves with the increase of information content or dimensionality of the collected data. Massive data generated during sensor operation leads to the need for effective data analysis and interpretation to identify trends and relationships within the collected data. Advanced mathematical and statistical chemometric techniques may be used in embodiments of the invention to determine the properties of substances that otherwise would be difficult to measure directly.

Pattern recognition techniques on collected signals from each wireless sensor may be utilized to find similarities and differences between measured data points. This approach provides a technique for warning of the occurrence of abnormalities in the measured data. These techniques can reveal correlated patterns in large data sets, can determine the structural relationship among screening hits, and can significantly reduce data dimensionality to make it more manageable in the database. Methods of pattern recognition include principal components analysis (PCA), hierarchical cluster analysis (HCA), soft independent modeling of class analogies (SIMCA), neural networks, and others known in the art.

Multivariate calibration methods offer several advantages over univariate calibration methods. Signal averaging is achieved since more than one measurement channel is employed in the analysis. Also, the concentrations of multiple species may be measured if they are present in the calibration samples. A calibration model is built by using responses from calibration standard solutions. The analysis of unknown samples will suffer if a species is present in the sample that is not accounted for in the calibration model. This is mitigated somewhat by the ability to detect whether a sample is an outlier from the calibration set. Multivariate calibration approaches permit selective quantitation of several analytes of interest in complex combinatorial libraries using low-resolution instruments when overlapping responses from different species preclude the use of univariate analysis.

EXAMPLE 4

Multiparameter Signal Detection

Figure 20:
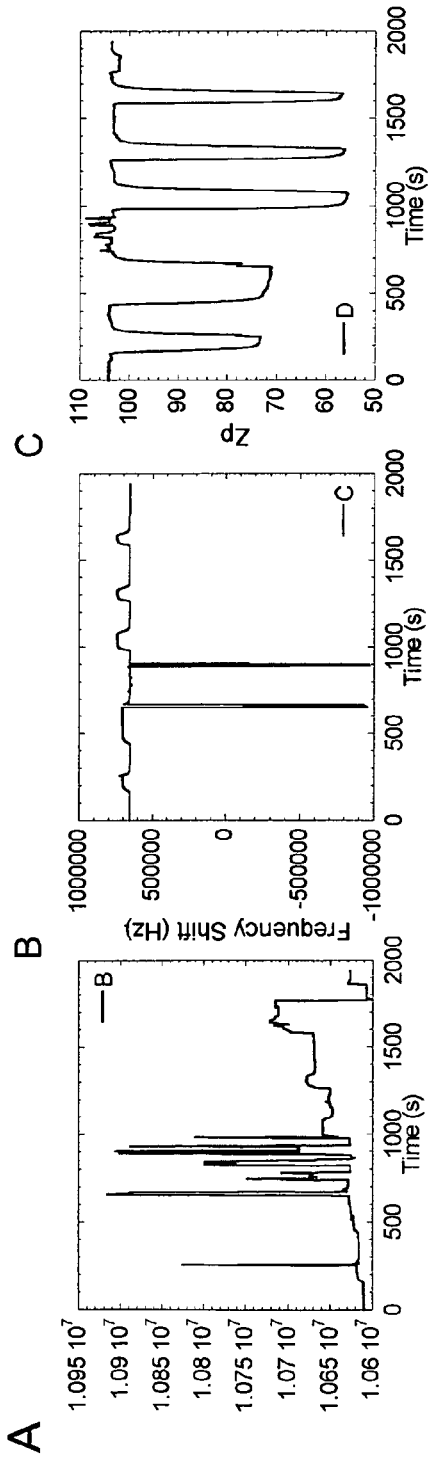
FIGS. 20A-C illustrate, respectively, the frequency shift, the peak width of imaginary signal component, and the peak intensity of the real signal component from an RFID tag constructed in accordance with an exemplary embodiment of the invention, immersed in water, and exposed to two replicates of 600 ppb of NaCl and three replicates of 1000 ppb of NaCl.

A passive wireless sensor with a nominal frequency of 13.5 MHz was immersed into water. Variable concentrations of NaCl were made and the wireless sensor was put in contact with about 600 and 1000 ppb of NaCl. Exposures were made in several replicates. Measurements were performed using a network analyzer. The network analyzer was used to measure three parameters from the wireless sensor. These parameters included frequency shift, peak width, and peak intensity as shown in FIGS. 20A-C, respectively.

Next, principal components analysis (PCA) was used to extract the desired descriptors from the dynamic data. PCA is a multivariate data analysis tool that projects the data set onto a subspace of lower dimensionality with removed colinearity. PCA achieves this objective by explaining the variance of the data matrix X in terms of the weighted sums of the original variables with no significant loss of information. These weighted sums of the original variables are called principal components (PCs). Upon applying the PCA, the data matrix X is expressed as a linear combination of orthogonal vectors along the directions of the principal components:

$$X = t_1 p^T_1 + t_2 p^T_2 + \ldots + t_A p^T_K + E \quad \text{(Equation 1)}$$

where $t_i$ and $p_i$ are, respectively, the score and loading vectors, K is the number of principal components, E is a residual matrix that represents random error, and T is the transpose of the matrix. Prior to PCA, data was appropriately preprocessed. The preprocessing included auto scaling.

Figure 21:
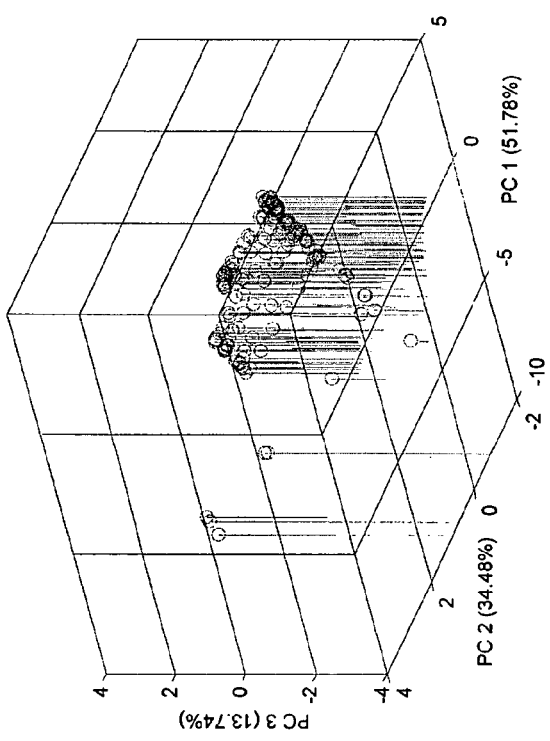
FIG. 21 illustrates results of multivariate analysis using an RFID tag constructed in accordance with an exemplary embodiment of the invention.
Figure 23:
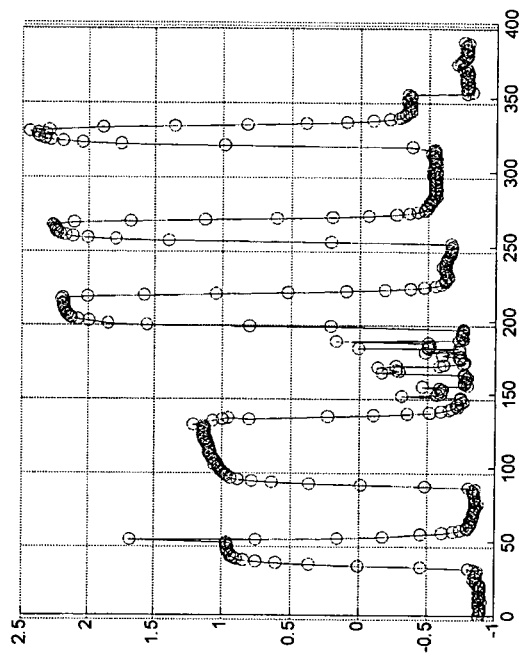
FIG. 23 illustrates principal component analysis results of first and second principal components as a function of experimental time depicting two replicates of 600 ppb NaCl and three replicates of 1000 ppb of NaCl.
Figure 22:
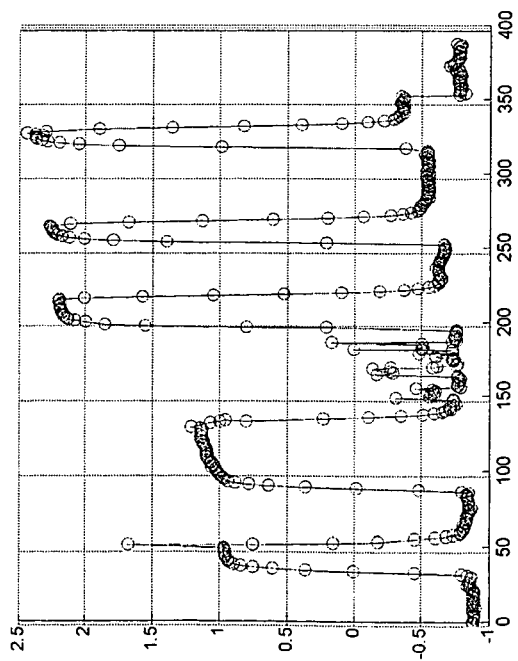
FIG. 22 illustrates principal component analysis results by plotting a second principal component as a function of experimental time depicting two replicates of 600 ppb NaCl and three replicates of 1000 ppb of NaCl.

Results of multivariate analysis are depicted in FIG. 21. A scores plot of three principal components of dynamic data shows a complex relation between measured signals from one sensor. This analysis permits an identification of main factors affecting the response of the sensor and related to the analyte response and interferences. FIG. 22 presents PCA results showing a plot of second principal component (PC) as a function of experimental time depicting two replicates of 600 ppb of NaCl and three replicates of 1000 ppb of NaCl. Based on the response of a single PC, it is difficult to determine the effects on the sensor. Thus, a combination of several responses of the wireless sensor is analyzed. FIG. 23 shows PCA results of first and second PCs as a function of experimental time depicting two replicates of 600 ppb of NaCl and three replicates of 1000 ppb of NaCl. Clearly, analysis of more than one response from a single sensor provides a desired discrimination between noise contributions and useful signal.

To ensure the quality of the wireless sensor data analyzed using multivariate tools, such as PCA, several statistical tools may be applied. These tools are multivariate control charts and multivariate contributions plots. Multivariate control charts use two statistical indicators of the PCA model, such as Hotelling's $T^2$ and Q values plotted as a function of combinatorial sample or time. The significant principal components of the PCA model are used to develop the $T^2$-chart and the remaining PCs contribute to the Q-chart. The sum of normalized squared scores, $T^2$ statistic, gives a measure of variation within the PCA model and determines statistically anomalous samples:

$$T^2 i = t i\, \lambda^{-1} t i^T = x i\, P\, \lambda^{-1} P^T x i^T \quad \text{(Equation 2)}$$

where $ti$ is the ith row of $Tk$, the matrix of k scores vectors from the PCA model, $\lambda^{-1}$ is the diagonal matrix containing the inverse of the eigenvalues associated with the K eigenvectors (principal components) retained in the model, $xi$ is the ith sample in X, and P is the matrix of K loadings vectors retained in the PCA model (where each vector is a column of P). The Q residual is the squared prediction error and describes how well the PCA model fits each sample. It is a measure of the amount of variation in each sample not captured by K principal components retained in the model:

$$Qi = ei\, ei^T = xi(I - Pk\, Pk^T) xi^T \quad \text{(Equation 3)}$$

where $ei$ is the ith row of E, and I is the identity matrix of appropriate size (n×n).

Figure 24:
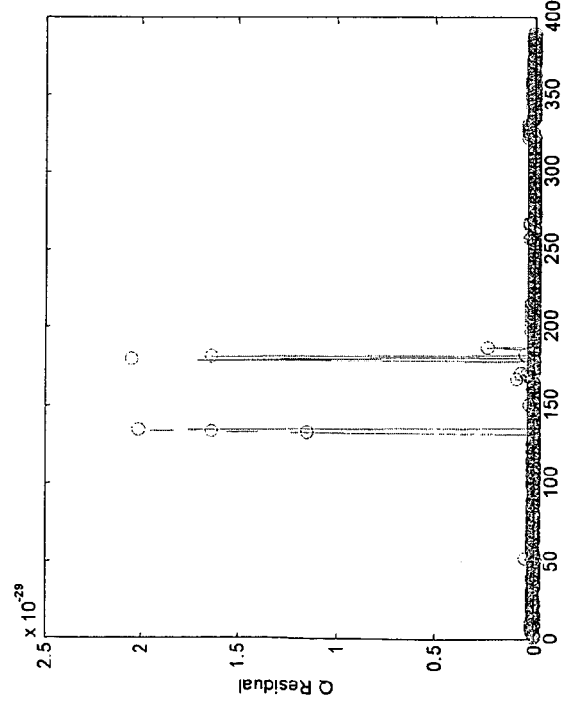
FIGS. 24A and 24B illustrate multivariate $T^2$ and Q statistics control charts for dynamic data from an RFID constructed in accordance with an exemplary embodiment of the invention.

The multivariate $T^2$ and Q statistics control charts for the dynamic data from the wireless sensor are presented in FIGS. 24A and 24B. These control charts illustrate that several data points exceed the 95% confidence limits for the $T^2$ and Q statistics described by the PCA model. The contributions plots of these statistical parameters can be used to track the origin of the largest contributors to these alarms.

EXAMPLE 5

Quantitative Response of an RFID Sensor at Different Positions Relative to the Receiver Antenna It has been found that a certain mathematical processing of the signals from a wireless, such as an RFID, sensor makes possible compensation for the repositioning differences in sensor sensitivity toward analytes. This certain mathematical processing enables a reader to report a response that is independent of the position of the sensor relative to the reader.

Figure 25:
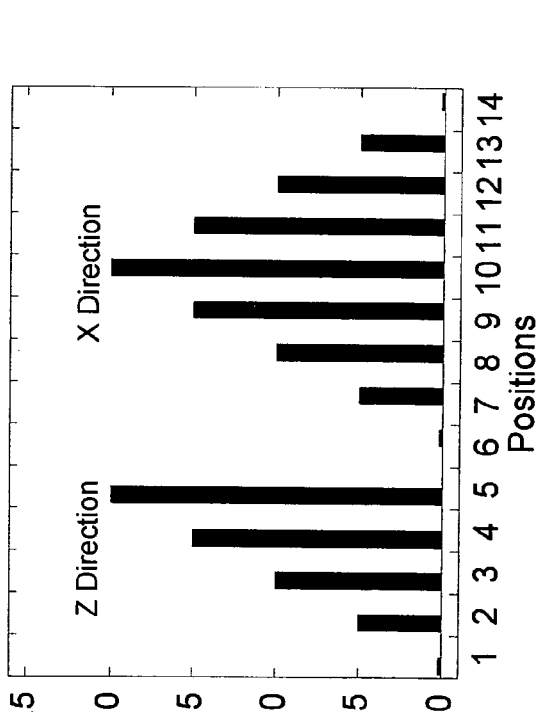
FIG. 25 illustrates different positions of an RFID sensor constructed in accordance with an embodiment of the invention in the X and Z direction with respect to the receiving antenna.

FIG. 25 illustrates the different tested positions of the RFID sensor in the X and Z direction with respect to the receiving antenna. The RFID sensor was coated with a polymer film responsive to water vapor. The sensing polymer sensitive to water vapor was prepared by dissolving poly (vinyl acetate) polymer in THF and adding 60% wt. of carbon black. The sensor film coating was applied onto the RFID tag and solvent was evaporated. The RFID sensor was posited into a flow cell. The flow cell was posited onto a X-Z stage with a receiver coil under the RFID sensor. For each position of the sensor, two replicate exposures to water vapor were performed where the water vapor was generated by bubbling dry nitrogen through water at room temperature and monitoring the relative humidity of the resulting gas. As a result, during each step, the sensor environment was switched twice from dry nitrogen to 45% relative humidity (RH) nitrogen.

Results of the analysis of response of the RFID sensor to the changes in RH at different distances from the receiving antenna are summarized in FIGS. 26A-D. The measured parameters included parameters from the real and imaginary portions of the complex impedance. In particular, frequency shift of the maximum of the imaginary part of the complex impedance is F1 shift, frequency shift of the minimum of the imaginary part of the complex impedance is F2 shift, frequency shift of the maximum of the real part of the complex impedance is Fp shift, and the magnitude of the real part of the complex impedance is Zp. FIG. 26A illustrates the change in F1 shift as a function of Z and X positions and replicate analyte exposures. Upon Z increase, the sensor baseline increases but the sensitivity to analyte decreases. Upon X increase, the sensor baseline slightly increases but the sensitivity to analyte does not significantly change. FIG. 26B illustrates the change in F2 shift as a function of Z and X positions and replicate analyte exposures. Upon Z increase, the sensor baseline decreases but the sensitivity to analyte increases. Upon X increase and decrease, the sensor baseline does not significantly change and the sensitivity to analyte does not significantly change. FIG. 26C illustrates the change in Fp shift as a function of Z and X positions and replicate analyte exposures. Upon Z increase, the sensor baseline increases but the sensitivity to analyte does not significantly change. Upon X increase and decrease, the sensor baseline slightly changes but the sensitivity to analyte does not significantly change. FIG. 26D illustrates the change in Zp shift as a function of Z and X positions and replicate analyte exposures. Upon Z increase, the sensor baseline decreases and the sensitivity to analyte decreases. Upon X increase, the sensor baseline slightly decreases but the sensitivity to analyte does not significantly change.

Figure 26:
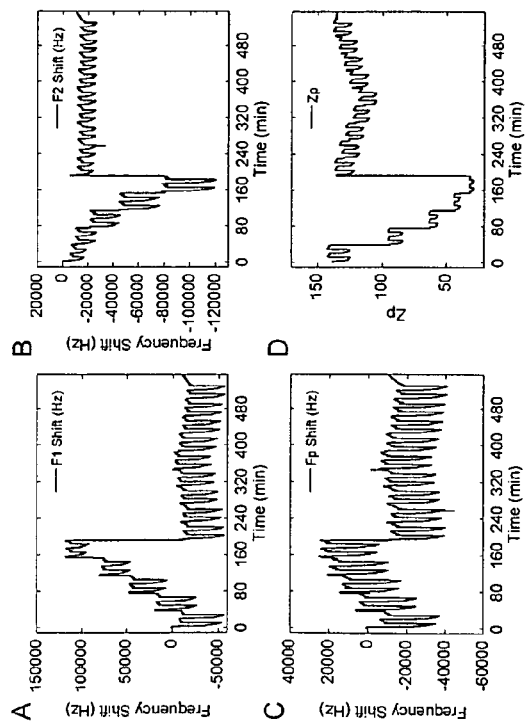
FIGS. 26A-D illustrate the response of an RFID sensor constructed in accordance with an embodiment of the invention to changes in relative humidity at different distances from the receiving antenna.
Figure 27:
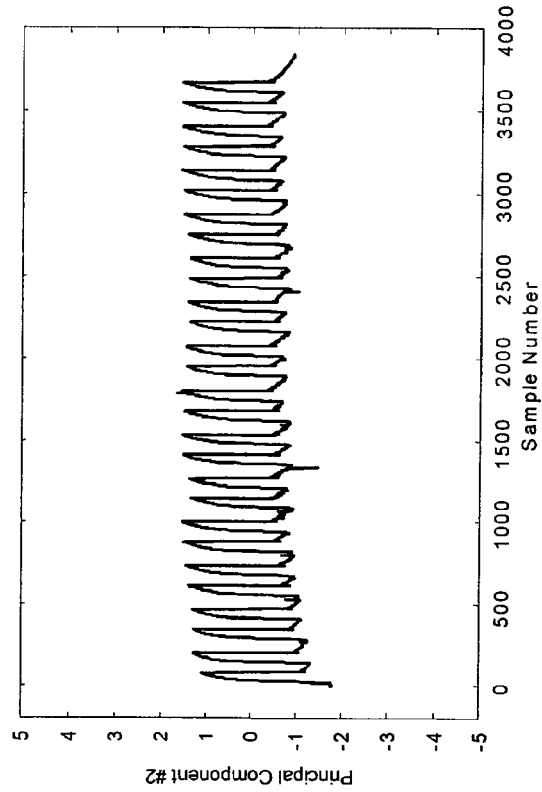
FIG. 27 illustrates a result of multivariate analysis of response of an RFID sensor constructed in accordance with an embodiment of the invention to changes in relative humidity at different distances from the receiving antenna.

Results of the multivariate analysis of response of the RFID sensor to the changes in RH at different distances from the receiving antenna are summarized in FIG. 27, with data applied in the analysis including the measured parameters shown in FIG. 26 A-D and calculated intrinsic parameters such as inductance L, capacitance C, resistance R, and quality factor Q of the antenna circuit. These intrinsic parameters are calculated using relationships known in the art. As shown in FIG. 27, similar sensitivity of the sensor is obtained by analyzing the sensor signal using multivariate analysis tools, where multiple features of the sensor response are employed for analysis. These features include the shape of the real and imaginary parts of the complex impedance of the RFID sensor as well its parameters such as Q, C, L, and R. The results illustrated in FIG. 27 indicate that embodiments of the invention are enabled to provide sensor-to-reader position independent responses.

Figure 28:
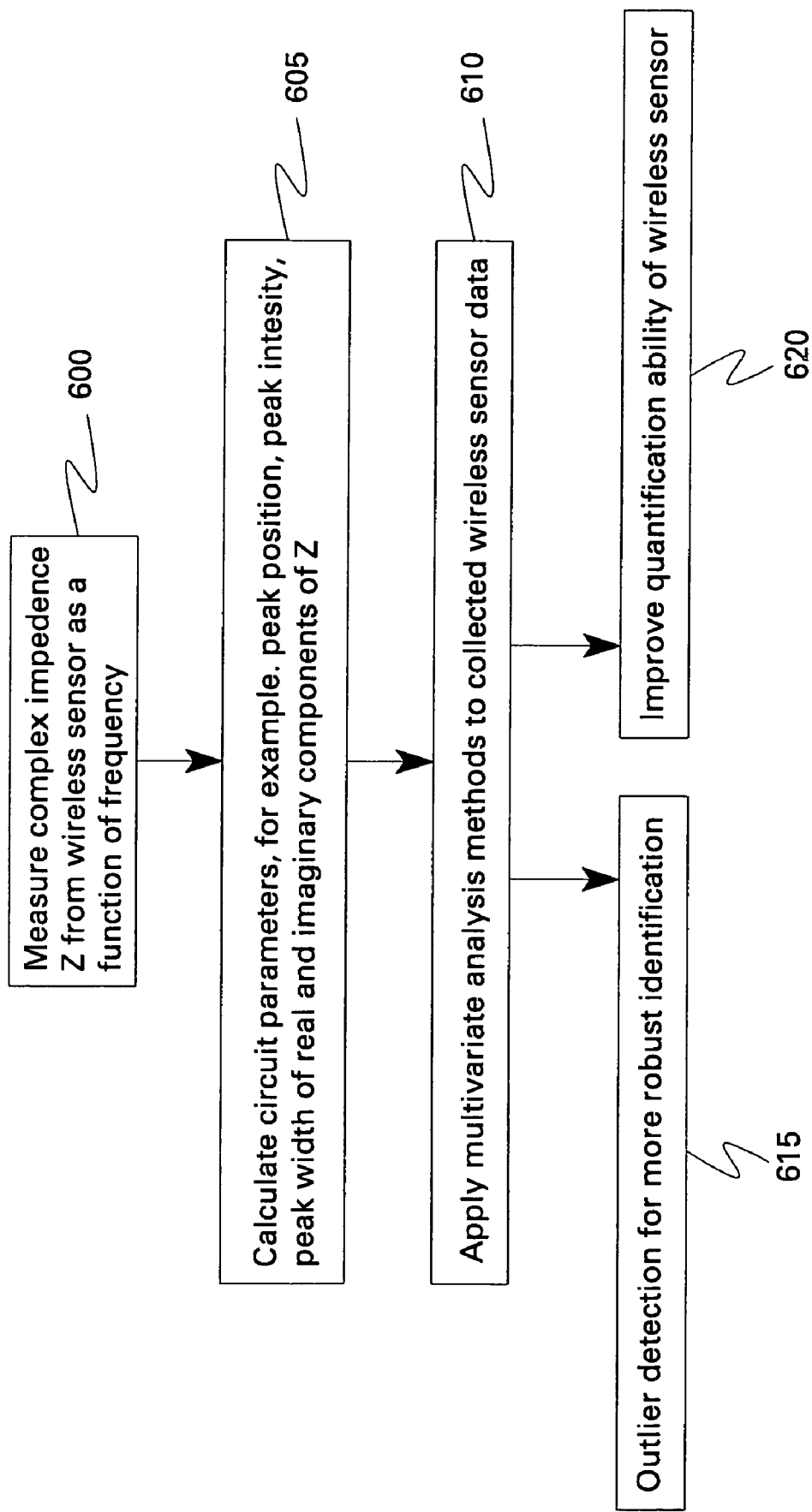
FIG. 28 illustrates method steps for utilizing an RFID tag constructed in accordance with an exemplary embodiment of the invention.

Referring now to FIG. 28, there is shown a method for using a wireless sensor, such as the wireless sensors illustrated in FIGS. 2-11. At Step 600, a complex impedance Z is measured from the wireless sensor as a function of frequency. At Step 605, circuit parameters are calculated. Examples of calculated circuit parameters include peak position, peak intensity, and peak width of real and imaginary components of the impedance Z. At Step 610, multivariate analysis methods are applied to the collected wireless sensor data. The multivariate analysis methods may include, for example, pattern recognition techniques such as principal components analysis (PCA), hierarchical cluster analysis (HCA), soft independent modeling of class analogies (SIMCA), and neural networks. At Step 615, outlier detection is performed to improve identification. Finally, at Step 620, improved quantification is enabled for the wireless sensor.

Figure 29:
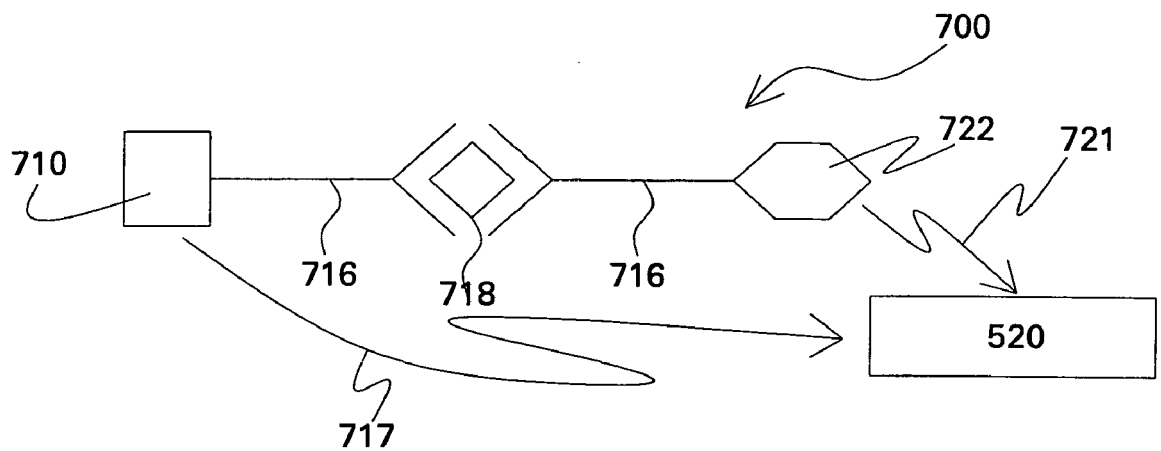
FIG. 29 illustrates a detection system constructed in accordance with an exemplary embodiment of the invention.
Figure 30:
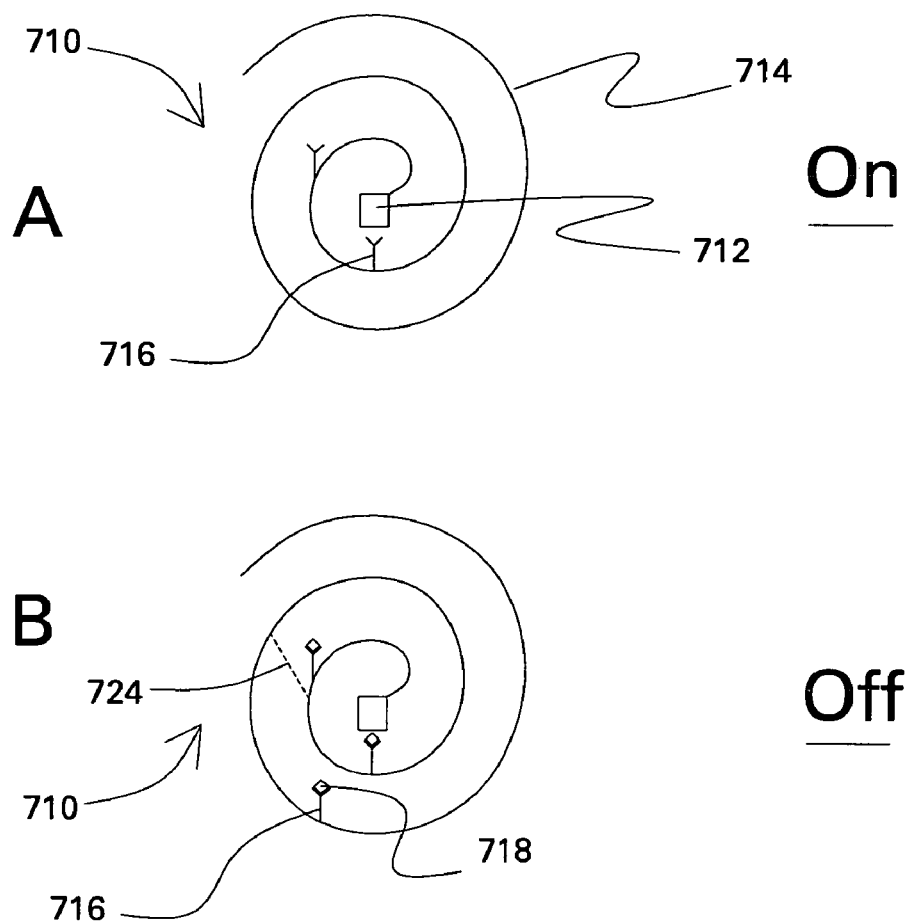
FIGS. 30A and 30B illustrate, respectively, ON and OFF states of an RFID tag constructed in accordance with an exemplary embodiment of the invention.
Figure 31:
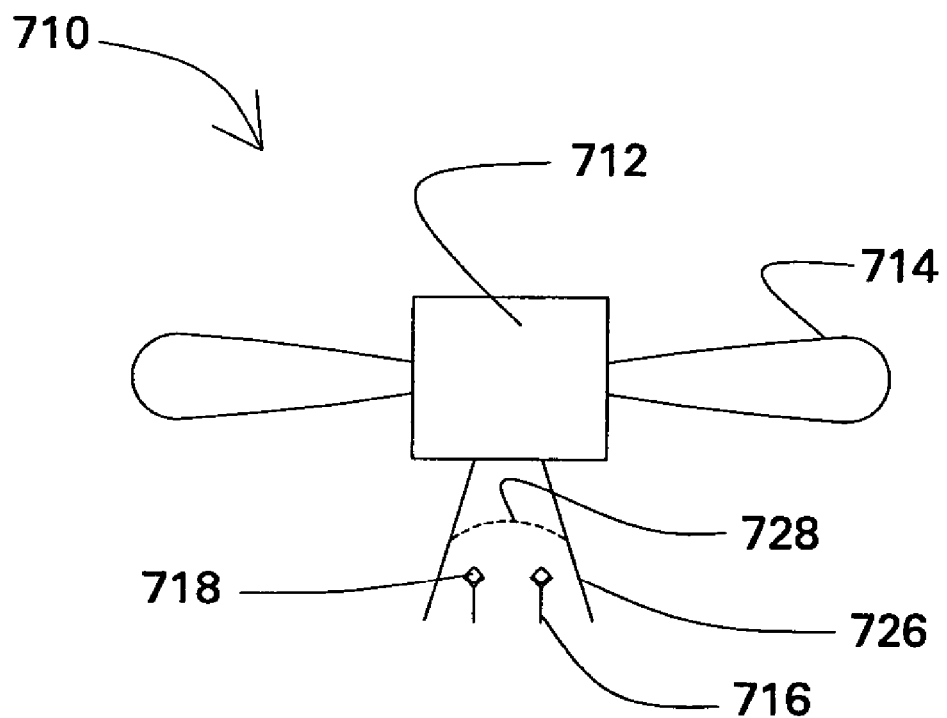
FIG. 31 illustrates an RFID tag constructed in accordance with an exemplary embodiment of the invention.

Referring now to FIGS. 29-31, there is shown a detection system 700. The detection system includes a wireless sensor, such as an RFID tag 710, a quantification tag 722, and the reader 520. The RFID tag 710 includes a substrate or chip 712 and an antenna 714 (FIG. 30). Further, one or more antibodies 716 are arrayed on the RFID tag 710. As illustrated in FIG. 30, the antibodies 716 are arrayed on the antenna 714, whereas as illustrated in FIG. 31, the antibodies 716 are arrayed within chip circuitry 726. The antibodies 716 serve to alter the signals emanating from the RFID tag 710, thereby turning the sensor ON or OFF.

The antibodies 716 arrayed on the RFID tag 710 are sensitive to a specific analyte. Hence, if you know the type of antibodies 716 arrayed on the RFID tag 710, then you will know the specific analyte attracted to the antibodies 716, and a signal 717 of the specific analyte 718 attracted to the antibodies 716 is transmitted to the reader 520. Further, the quantification tag 722 also includes antibodies 716, which will attract the same specific analyte 718 as the antibodies 716 attached to the RFID tag 710. The quantification tag 722 will enable the quantification of the amount of analyte 718 detected by the detection system 700, and a signal 721 of that quantification is transmitted to the reader 520. The quantification tag 722 may be any suitable tagging technique that will involve identification including, for example, fluorescence, absorbance, or RAMAN.

With specific reference to FIGS. 30A and 30B, next will be described a technique for turning an RFID tag to the ON or OFF state. As illustrated in FIG. 30A, antibodies 716 are arrayed along the antenna 714. The signal emanating from the RFID tag 710 is within the wavelength detectable by the reader 520 (FIG. 29). As the specific analyte 718 is attracted to the antibodies 716, the attraction leads to an electrical short 724 in the antenna 714, thereby altering the signal emanating from the RFID tag 710. The altered signal is outside the wavelength detectable by the reader 520, thereby altering the state of the RFID tag from the ON state (FIG. 30A) to the OFF state (FIG. 30B). Alternatively, the RFID tag 710 may be configured such that the tag is initially in the OFF state (the emanating signal is outside the detectable wavelength of the reader 520 prior to the attachment of the specific analyte 718 to the antibodies 716), and the electrical short 724 turns the RFID tag 710 to the ON state by altering the signal to be within the detectable wavelength of the reader 520.

Alternatively, and with specific reference to FIG. 31, antibodies 716 are arrayed on circuitry 726 of the RFID tag 710. The attraction of the specific analyte 718 to the antibodies 716 causes an electrical short 728 in the circuitry 726, which causes a different signal to emanate from the antenna 714 of the RFID tab 710. If the initial signal was within the detectable wavelength of the reader 520 (ON state), then the electrical short 728 would change the RFID tag 710 to the OFF state. Conversely, if the initial signal was outside of the detectable wavelength of the reader 520 (OFF state), then the electrical short 728 would change the RFID tag 710 to the ON state.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. A detection system utilizing at least one radiofrequency identification (RFID) tag, comprising:
   an RFID tag comprising;
   a substrate;
   an antenna is disposed on said substrate;
   a sensor material disposed adjacent to at least a portion of the antenna and the sensor material being selected to be sensitive to one of chemical or biological environment; and
   a reader for receiving and processing signals from said RFID tag, wherein said reader is configured to measure a signal in the form of a complex impedance from said RFID tag wherein said signal comprises a plurality of frequency shifts and changes in magnitude of the and imaginary parts of the complex impedance to provide position independent responses from said RFID tag;
   wherein said frequency shifts comprise a frequency shift of the maximum of the imaginary part of the complex impedance (F1 shift), a frequency shift of the minimum of the imaginary part of the complex impedance (F2 shift), a frequency shift of the maximum part of the complex impedance (Fp), and changes in magnitude of the real part of the complex impedance (Zp); and,
   wherein said complex impedance related to a nature and a concentration of analyte species is derived from multivariate analysis.

2. The detection system of claim 1, wherein said reader includes a multivariate pattern recognition subcomponent.

3. The detection system of claim 1, wherein the reader is configured to periodically read and quantify the signal from the RFID tag.

4. The detection system of claim 1, wherein the sensor material is sensitive to a biospecific entity.

5. A detection system insensitive to repositioning of the sensor reader in relation to the RF wireless sensor, comprising;
   an RF wireless sensor;
   a sensor reader configured to transmit RF energy to said RF wireless sensor, configured to receive and process signals from said RF wireless sensor, and configured to measure a plurality of frequency shifts and changes in magnitude corresponding to real and imaginary parts of the complex impedance of said RF wireless sensor at least three frequencies, wherein said frequency shifts comprise a frequency shift of the maximum of the imaginary part of the complex impedance (F1 shift), a frequency shift of the minimum of the imaginary art of the complex impedance (F2 shift), a frequency shift of the maximum part of the complex impedance (Fp); and
   a multivariate signal processor that derives the concentration of species of interest from multivariate analysis of the measured and computed parameters of frequency shifts and changes in magnitude comprises a frequency shift of the maximum of the imaginary part of the complex impedance (F1 shift), a frequency shift of the minimum of the imaginary part of the complex impedance (F2 shift), a frequency shift of the maximum part of the complex impedance (Fp), and a magnitude of the real part of the complex impedance (Zp), and provides quantification of the species independent of the relative position of said sensor reader in relation to said RF wireless sensor.

6. The detection system of claim 5, wherein said sensor reader is configured to measure at least two parameters from which a signal, related to a nature and a concentration of analyte species, is derived.

7. The detection system of claim 6, wherein said signal is derived from multivariate analysis of the at least two parameters.

8. The detection system of claim 5, wherein said RF wireless sensor comprises:
   a substrate;
   an antenna disposed on said substrate; and
   a sensor material sensitive to a biospecific or chemical entity disposed over at least a portion of said substrate.

* * * * *